(12) United States Patent
Reed et al.

(10) Patent No.: US 8,148,167 B2
(45) Date of Patent: *Apr. 3, 2012

(54) FLUORESCENT PH DETECTOR SYSTEM AND RELATED METHODS

(75) Inventors: Michael W. Reed, Lake Forest Park, WA (US); Steven J. Geelhood, Seattle, WA (US); Paul C. Harris, Bothell, WA (US); Randy D. Pfalzgraf, Snohomish, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,073

(22) Filed: Jun. 2, 2011

(65) Prior Publication Data
US 2011/0236988 A1    Sep. 29, 2011

Related U.S. Application Data

(60) Continuation of application No. 12/572,566, filed on Oct. 2, 2009, now Pat. No. 7,968,346, which is a division of application No. 11/207,580, filed on Aug. 19, 2005, now Pat. No. 7,608,460.

(60) Provisional application No. 60/674,393, filed on Apr. 22, 2005, provisional application No. 60/602,684, filed on Aug. 19, 2004.

(51) Int. Cl.
*G01N 31/16* (2006.01)
*G01N 31/22* (2006.01)
*G01N 21/76* (2006.01)
*G01N 21/64* (2006.01)
*G01N 21/66* (2006.01)
*C12Q 1/02* (2006.01)

(52) U.S. Cl. ........ 436/163; 436/172; 435/29; 422/82.08

(58) Field of Classification Search .................. 436/163, 436/179; 435/29
See application file for complete search history.

(56) References Cited

U.S. PATENT DOCUMENTS

| | | |
|---|---|---|
| 2,136,236 A | 11/1938 | Draper |
| 2,856,885 A | 10/1958 | Huyck et al. |
| 2,856,930 A | 10/1958 | Huyck et al. |
| 2,890,177 A | 6/1959 | Kilmer |
| 3,068,073 A | 12/1962 | Stanford |
| 3,754,867 A | 8/1973 | Guenther |

(Continued)

FOREIGN PATENT DOCUMENTS
DE      41 08 808 A1    9/1992

(Continued)

OTHER PUBLICATIONS

Aizawa, M., et al., "Molecular Assembling Technology for Electrochemical and Optical Enzyme-Sensing Films," *IEEE International Conference on Solid-State Sensors and Actuators, Digest of Technical Papers*, San Francisco, Jun. 24-27, 1991, pp. 68-73.

(Continued)

*Primary Examiner* — Sam P Siefke
*Assistant Examiner* — Bryan Kilpatrick
(74) *Attorney, Agent, or Firm* — Christensen O'Connor Johnson Kindness PLLC

(57) ABSTRACT

Fluorescent pH detector and methods for measuring pH using the fluorescent pH detector.

23 Claims, 23 Drawing Sheets

U.S. PATENT DOCUMENTS

| | | | |
|---|---|---|---|
| 4,116,336 A | 9/1978 | Sorensen et al. | |
| 4,200,110 A | 4/1980 | Peterson et al. | |
| 4,655,763 A | 4/1987 | Malcolm et al. | |
| 4,666,672 A | 5/1987 | Miller et al. | |
| 4,691,701 A | 9/1987 | Williams | |
| 4,728,499 A | 3/1988 | Fehder | |
| 4,743,629 A | 5/1988 | Karakelle et al. | |
| 4,746,751 A | 5/1988 | Oviatt, Jr. et al. | |
| 4,785,814 A | 11/1988 | Kane | |
| 4,861,130 A | 8/1989 | Katsuyama et al. | |
| 4,892,383 A | 1/1990 | Klainer et al. | |
| 4,917,491 A | 4/1990 | Ring et al. | |
| 4,945,060 A | 7/1990 | Turner et al. | |
| 4,945,171 A | 7/1990 | Haugland et al. | |
| 5,094,955 A | 3/1992 | Calandra et al. | |
| 5,114,864 A | 5/1992 | Walt | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,223,224 A | 6/1993 | Dremel et al. | |
| 5,238,809 A | 8/1993 | Wolfbeis | |
| 5,401,376 A | 3/1995 | Foos et al. | |
| 5,408,999 A | 4/1995 | Singh et al. | |
| 5,489,536 A | 2/1996 | Ekechukwu | |
| 5,495,850 A | 3/1996 | Zuckerman | |
| 5,515,864 A | 5/1996 | Zuckerman | |
| 5,518,895 A | 5/1996 | Thorpe et al. | |
| 5,595,187 A | 1/1997 | Davis | |
| 5,605,809 A | 2/1997 | Komoriya et al. | |
| 5,607,644 A | 3/1997 | Olstein et al. | |
| 5,672,515 A | 9/1997 | Furlong | |
| 5,770,705 A | 6/1998 | Shanbrom | |
| 5,795,773 A | 8/1998 | Read et al. | |
| 5,814,524 A | 9/1998 | Walt et al. | |
| 5,856,175 A | 1/1999 | Thorpe et al. | |
| 5,858,769 A | 1/1999 | DiGuiseppi et al. | |
| 5,900,215 A | 5/1999 | Seifert et al. | |
| 6,204,067 B1 | 3/2001 | Simon et al. | |
| 6,210,910 B1 | 4/2001 | Walt et al. | |
| 6,266,459 B1 | 7/2001 | Walt et al. | |
| 6,268,910 B1 | 7/2001 | Samsoondar et al. | |
| 6,271,039 B1 | 8/2001 | Palmer et al. | |
| 6,285,807 B1 | 9/2001 | Walt et al. | |
| 6,315,767 B1 | 11/2001 | Dumont et al. | |
| 6,377,721 B1 | 4/2002 | Walt et al. | |
| 6,391,626 B1 | 5/2002 | Adams et al. | |
| 6,544,727 B1 | 4/2003 | Hei | |
| 6,558,546 B2 | 5/2003 | Allcock et al. | |
| 6,602,716 B1 | 8/2003 | Klimant | |
| 6,636,652 B1 | 10/2003 | Kopelman et al. | |
| 6,667,159 B1 | 12/2003 | Walt et al. | |
| 6,673,532 B2 | 1/2004 | Rao | |
| 6,684,680 B2 | 2/2004 | Pierskalla et al. | |
| 6,694,157 B1 | 2/2004 | Stone et al. | |
| 6,726,671 B2 | 4/2004 | Dumont et al. | |
| 6,727,356 B1 | 4/2004 | Reed et al. | |
| 6,738,651 B1 | 5/2004 | Jackson | |
| 6,777,226 B2 | 8/2004 | Jeffrey et al. | |
| 6,790,672 B2 | 9/2004 | Balkus, Jr. et al. | |
| 6,800,765 B2 | 10/2004 | Diwu et al. | |
| 6,859,570 B2 | 2/2005 | Walt et al. | |
| 6,861,954 B2 | 3/2005 | Levin | |
| 7,608,460 B2 * | 10/2009 | Reed et al. | 436/163 |
| 7,968,346 B2 * | 6/2011 | Reed et al. | 436/163 |
| 2001/0018217 A1 | 8/2001 | Barnard et al. | |
| 2001/0024800 A1 | 9/2001 | Garcia-Rubio et al. | |
| 2002/0012923 A1 | 1/2002 | Barenholz et al. | |
| 2002/0040216 A1 | 4/2002 | Dumont et al. | |
| 2002/0076819 A1 | 6/2002 | Bowman et al. | |
| 2002/0186363 A1 | 12/2002 | Samsoondar et al. | |
| 2003/0221477 A1 | 12/2003 | Pierskalla et al. | |
| 2004/0013569 A1 | 1/2004 | Balkus, Jr. et al. | |
| 2004/0044326 A1 | 3/2004 | Kranz et al. | |
| 2004/0047769 A1 | 3/2004 | Tanaami | |
| 2004/0058453 A1 | 3/2004 | Free et al. | |
| 2004/0166024 A1 | 8/2004 | Klimant | |
| 2004/0166583 A1 | 8/2004 | De Gaulle et al. | |
| 2004/0175836 A1 | 9/2004 | Klimant | |
| 2004/0206658 A1 | 10/2004 | Hammerstedt et al. | |
| 2004/0230337 A1 | 11/2004 | De Gaulle et al. | |
| 2005/0090014 A1 | 4/2005 | Rao et al. | |
| 2005/0176066 A1 | 8/2005 | Lukhtanov et al. | |
| 2006/0204990 A1 | 9/2006 | Lukhtanov et al. | |

FOREIGN PATENT DOCUMENTS

| | | |
|---|---|---|
| EP | 0 073 558 A2 | 3/1983 |
| EP | 0 354 719 A1 | 2/1990 |
| EP | 0 570 938 A2 | 11/1993 |
| EP | 0 601 816 A2 | 6/1994 |
| EP | 1 122 535 A2 | 8/2001 |
| FR | 2 825 637 A1 | 12/2002 |
| JP | 01227964 A | 9/1989 |
| JP | 2001194304 A | 7/2001 |
| WO | 92/19150 A1 | 11/1992 |
| WO | 98/40469 A1 | 9/1998 |
| WO | 98/58215 A1 | 12/1998 |
| WO | 02/054969 A1 | 7/2002 |
| WO | 2004/037308 A1 | 5/2004 |
| WO | 2006/023725 A2 | 3/2006 |

OTHER PUBLICATIONS

Andersson, R.M., et al., "Characterization of Probe Binding and Comparison of Its Influence on Fluorescence Lifetime of Two pH—Sensitive Benzo[C]xanthene Dyes Using Intensity-Modulated Multiple-Wavelength Scanning Technique," *Analytical Biochemistry* 283(1):104-110, Jul. 2000.

Baker, G.A., et al., "Assessment of One- and Two-Photon Excited Luminescence for Directly Measuring $O_2$, pH, $Na^+$, $Mg^{2+}$, or $Ca^{2+}$ in Optically Dense and Biologically Relevant Samples," *Applied Spectroscopy* 56(4):455-463, Apr. 2002.

Berthois, Y., et al., "Estradiol Membrane Binding Sites on Human Breast Cancer Cell Lines. Use of a Fluorescent Estradiol Conjugate to Demonstrate Plasma Membrane Binding Systems," *Journal of Steroid Biochemistry* 25(6):963-972, 1986.

Haugland, R.P., *Handbook of Fluorescent Probes and Research Products*, 9th ed., Molecular Probes, Inc., Eugene, Oregon, 2002, Chapter 21, "pH Indicators," pp. 827-848.

Hirshfield, K.M., et al., "Steady-State and Time-Resolved Fluorescence Measurements for Studying Molecular Interactions: Interaction of a Calcium-Binding Probe With Proteins", *Biophysical Chemistry* 62(1-3):25-38, Nov. 1996.

Jiang, D., et al., "A Novel Fiber Optic Glucose Biosensor Based on Fluorescence Quenching," *Proceedings of SPIE (The International Society for Optical Engineering USA) Advanced Sensor Systems and Applications* 4902:205-212, Sep. 2002.

Lee, L.G., et al., "Vita Blue: A New 633-nm Excitable Fluorescent Dye for Cell Analysis," *Cytometry* 10(2):151-164, Mar. 1989.

Matsumoto, H., et al., "Interaction of Proteins With Weak Amphoteric Charged Membrane Surfaces: Effect of pH," *Journal of Colloid and Interface Science* 264(1):82-88, Aug. 2003.

Nullmeyer, K.D., et al., "Extending the Range of Intracellular pH Measurements Using Fluorescent Probe Combinations," *FASEB Journal* 16(5):A797, Mar. 2002 (Abstract 621.10).

Patel, P.D., "(Bio)sensors for Measurement of Analytes Implicated in Food Safety: A Review," *Trends in Analytical Chemistry* 21(2):96-115, Feb. 2002.

Rao, J.K., et al., "Implantable Controlled Delivery System for Proteins Based on Collagen—pHEMA Hydrogels," *Biomaterials* 15(5):383-389, Apr. 1994.

Reichert, U., et al., "Visualising Protein Adsorption to Ion-Exchange Membranes by Confocal Microscopy," *Journal of Membrane Science* 199(1-2):161-166, Apr. 2002.

Sinaasappel, M., and C. Ince, "Calibration of Pd-Porphyrin Phosphorescence for Oxygen Concentration Measurements In Vivo," Journal of *Physiology* 81(5):2297-2303, Nov. 1996.

Slavik, J., et al., "Measurement of Individual Intracellular pH and Membrane Potential Values in Living Cells," *Proceedings of SPIE (The International Society for Optical Engineering), Biomedical Imaging: Reporters, Dyes, and Instrumentation* 3600:76-83, Jan. 1999.

Srivastava, A., and G. Krishnamoorthy, "Time-Resolved Fluorescence Microscopy Could Correct for Probe Binding While Estimating Intracellular pH," *Analytical Biochemistry 249*(2):140-146, Jul. 1997.

Turner, P., et al., "Measuring the Heterogeneity of Protein Loading in PLG Microspheres Using Flow Cytometry," *Journal of Controlled Release 96*(1):193-205, Apr. 2004.

Ulbricht, M., and M. Riedel, "Ultrafiltration Membrane Surfaces With Grafted Polymer 'Tentacles': Preparation, Characterization and Application for Covalent Protein Binding," *Biomaterials 19*(14):1229-1237, Jul. 1998.

Wetzel, C.H.R., et al., "Functional Antagonism of Gonadal Steroids at the 5-Hydroxytryptamine Type 3 Receptor," *Molecular Endocrinology 12*(9):1441-1451, Sep. 1998.

Whitaker, J.E., et al., "Seminaphtho-Fluoresceins and -Rhodafluors: Dual Florescence pH Indicators," *Biophysical Journal 53*:197a, 1988 (Abstract M-Pos 369).

Whitaker, J.E., et al., "Spectral and Photophysical Studies of.Benzo[c]xanthene Dyes: Dual Emission pH Sensors," *Analytical Biochemistry 194*(2):330-344, May 1991.

Wolfbeis, O.S., et al., "LED-Compatible Fluorosensor for Measurement of Near-Neutral pH Values," *Mikrochimica Acta 108*(3-6):133-141, May 1992.

Xu, Z., et al., "A Novel Fiber-Optic pH Sensor Incorporating Carboxy SNAFL-2 and Fluorescent Wavelength-Ratiometric Detection," *Journal of Biomedical Materials Research 39*(1):9-15, 1998.

* cited by examiner

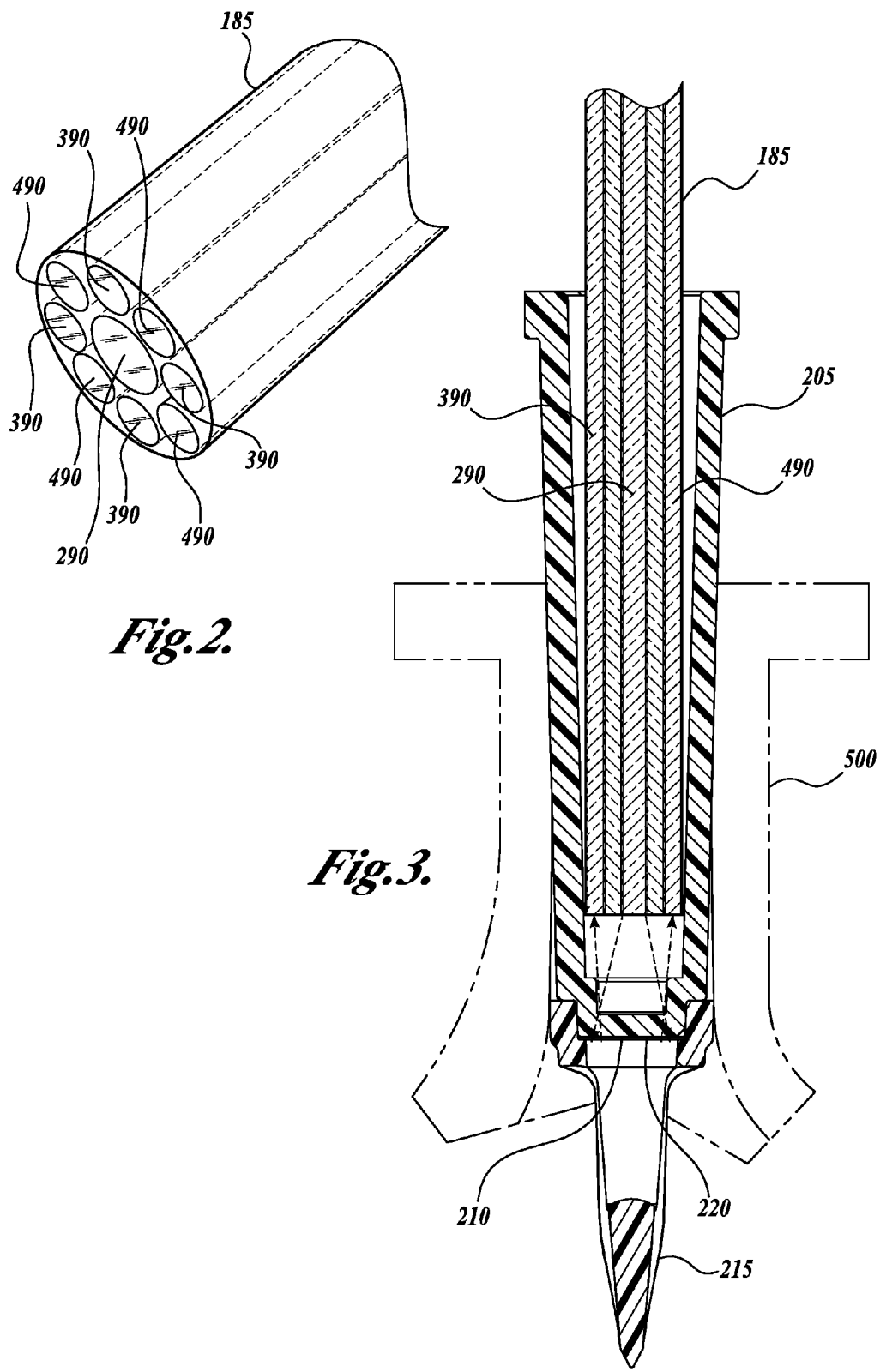

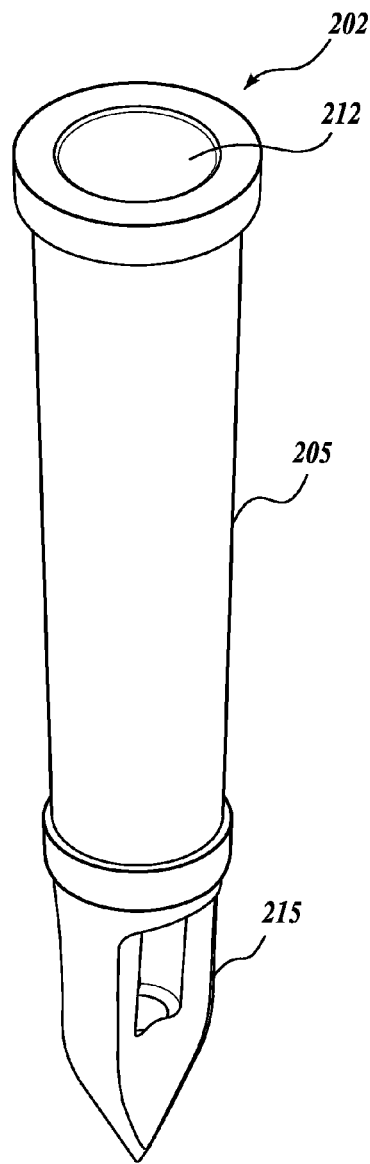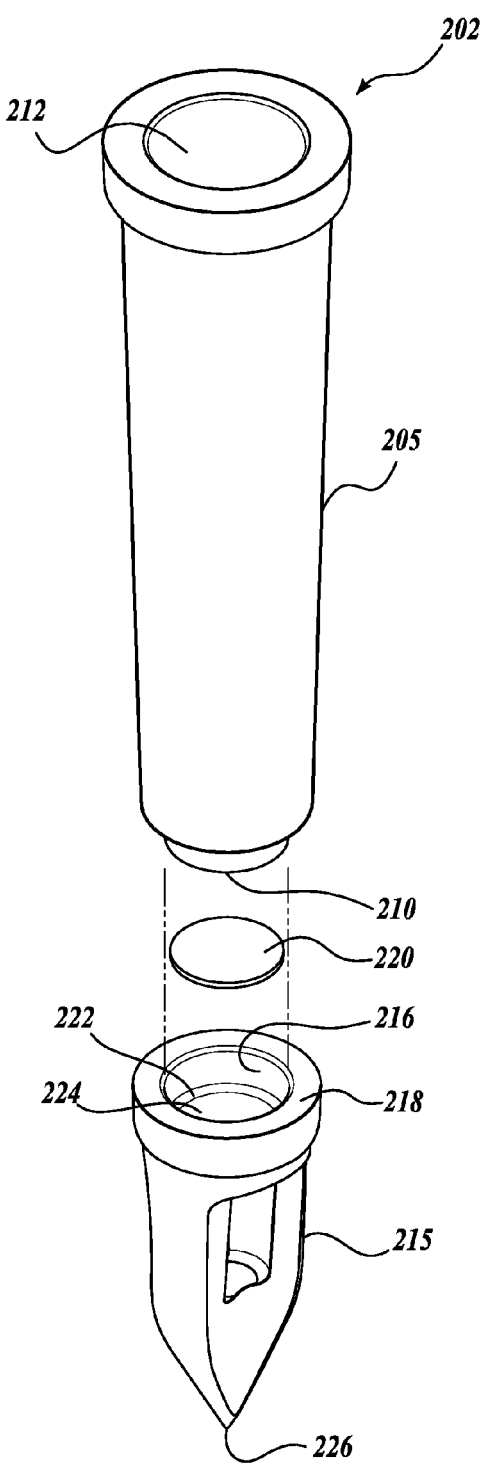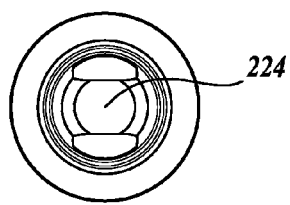
*Fig.4A.*
*Fig.4C.*
*Fig.4B.*

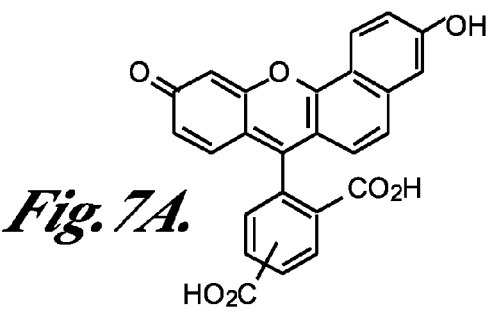
*Fig. 7A.*
SNAFL-1
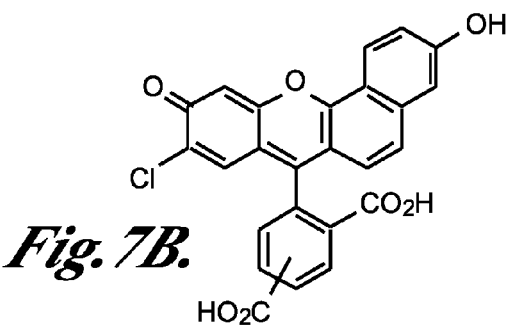
*Fig. 7B.*
SNAFL-2
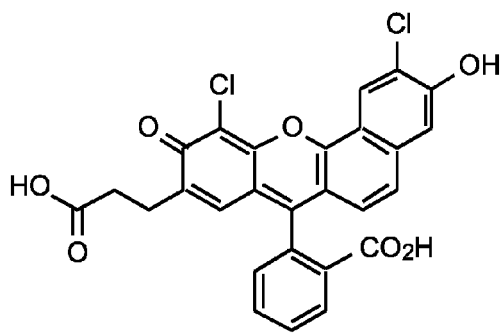
*Fig. 7C.* EBIO-1
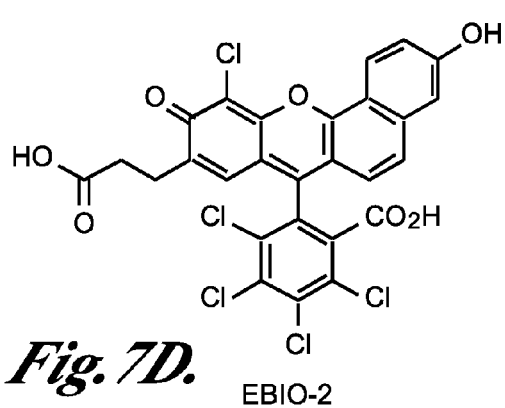
*Fig. 7D.* EBIO-2
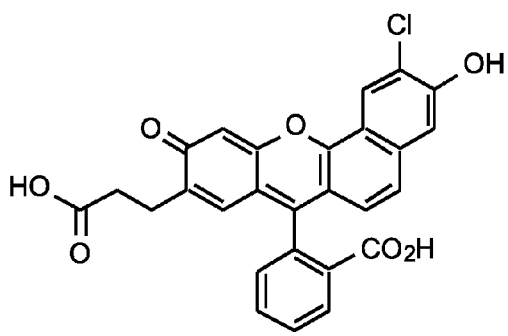
*Fig. 7E.* EBIO-3

FLUORESCENT PH DETECTOR SYSTEM AND RELATED METHODS

CROSS-REFERENCE TO RELATED APPLICATIONS

This application is a continuation of U.S. patent application Ser. No. 12/572,566, filed Oct. 2, 2009, now U.S. Pat. No. 7,968,346, which is a division of U.S. patent application Ser. No. 11/207,580, filed Aug. 19, 2005, now U.S. Pat. No. 7,608,460, which claims the benefit of U.S. Patent Application No. 60/674,393, filed Apr. 22, 2005, and U.S. Patent Application No. 60/602,684, filed Aug. 19, 2004. Each application is expressly incorporated herein by reference in its entirety.

FIELD OF THE INVENTION

The present invention relates to a fluorescent pH detector and methods for measuring pH using the fluorescent pH detector.

BACKGROUND OF THE INVENTION

Optical sensors (optrodes) for measuring pH are well known. Certain aromatic organic compounds (like phenolphthalein) change color with pH and can be immobilized on solid supports to form "pH paper." These visual indicators are easy to use, but do not provide a quantitative reading. The color changes can be difficult to distinguish accurately, and can be masked by colored analyte. Fluorescent indicators have also been used as optical sensors. pH Sensitive fluorescent dyes can be immobilized on solid supports and generally are more sensitive in comparison to the simple color changing (absorbance or reflectance based) indicators. The improved sensitivity of fluorescent indicators allows the solid support to be miniaturized, and this has been used to advantage in development of fiber optic sensor devices for measuring pH, $CO_2$, and $O_2$ parameters in blood.

A specific need in the medical industry exists for accurate pH measurement of blood. The pH of blood, or other bodily fluids (pleural effusions) can be associated with certain physiologic responses associated with pathology. Blood gas analyzers are common critical care instruments. Depending on storage conditions, the pH of separated blood components (plasma, platelets) can change rapidly due to off-gassing of dissolved $CO_2$ from the enriched venous blood that is collected from a donor. Platelets in particular are metabolically active, and generate lactic acid during storage at 20-22° C. European quality guidelines for platelets prepared by the "buffycoat method" require pH of stored platelets to be pH 6.8-7.4 at 37° C. (7.0-7.6 at 22° C.).

Seminaphthofluorescein (SNAFL) compounds and the related seminaphthorhodafluor (SNARF) compounds are commercially available ratiometric fluors (Molecular Probes, Inc., Eugene, Oreg.; see, for example, U.S. Pat. No. 4,945,171) and their synthesis and spectral properties have been described. These compounds have advantages including long wavelength absorbance that can be efficiently excited with LED light sources. Relevant acid/base equilibria and associated spectral properties are shown below.

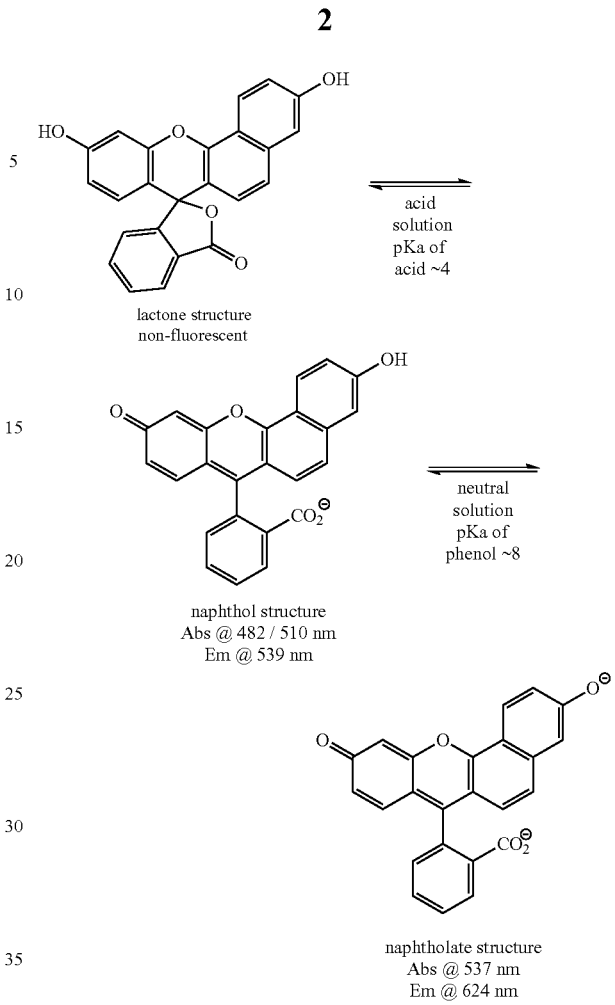

Deprotonation of the naphthol structure of SNAFL dyes gives a naphtholate molecule with longer wavelength fluorescence emission. The pKa is the pH value where the two molecular species form in equal amounts. SNAFL compounds with reactive linker groups that allow their conjugation to other molecules of interest are also commercially available.

Various methods have been used to immobilize "ratiometric" dyes to solid supports for use in fiber optic pH detectors. Carboxynaphthofluorescein (CNF) has been conjugated to aminoethyl-cellulose and this material was glued to polyester (Mylar) films to make sensing membranes for optrodes. The pKa of this material was 7.41, slightly lower than the free CNF (pKa 7.62). The use of tetraethoxysilane to trap CNF in a sol-gel glass that was formed on glass cover slips has also been reported. The pKa of this material was 7.46. A 9-chloro substituted SNAFL analog (SNAFL-2) has been reacted with polyvinylamine and the residual amino groups were crosslinked with a photocrosslinker to form a gel-like coating on acrylic fibers. The pKa of this fiber-optic sensor was 7.14, significantly lower than the published pKa of the free SNAFL compound (pKa ~7.7). This shows that molecular environment and linker structure surrounding the immobilized dye can alter the performance of a pH detector.

Despite the advances made in the detection of pH noted above, there exists a need for improved methods and devices for measuring pH. The present invention seeks to fulfill this need and provides further related advantages.

SUMMARY OF THE INVENTION

In one aspect, the present invention provides a method for measuring the pH of a sample. The method is useful in measuring the pH of blood and blood products. In one embodiment, the method is useful in measuring the pH of blood or blood products sealed in a vessel. In one embodiment, the method includes the steps of:

(a) irradiating a fluorescent species immobilized on a substrate with excitation light emanating from a probe physically isolated from the fluorescent species immobilized on the substrate, wherein the fluorescent species immobilized on the substrate is in liquid communication with a sample, wherein the excitation light has a wavelength sufficient to effect fluorescent emission from the fluorescent species, wherein the fluorescent species exhibits a first emission intensity at a first emission wavelength and a second emission intensity at a second emission wavelength, the ratio of the first and second emission intensities being dependent on pH; and (b) measuring the first and second emission intensities to determined the pH of the sample.

In the method, the probe is physically isolated from the fluorescent species immobilized on the substrate. As used herein, the term "physically isolated" refers to the physical isolation of the probe from the sample being interrogated. The probe providing excitation light and receiving emission light does contact the sample being interrogated. In the method of the invention, the sample is in contact (i.e., liquid communication) with the substrate-immobilized fluorescent species. The probe is isolated from and does not come not physical contact with the sample. The isolation of the probe from the sample is illustrated in FIGS. 3 and 5. In one embodiment, the probe is isolated from the fluorescent species by a window transparent to the excitation light and the fluorescent emission.

In one embodiment, the probe comprises one or more optical fibers.

In the method, the fluorescent species is a ratiometric fluorescent species. In one embodiment, the fluorescent species is selected from a naphthofluorescein compound and a seminaphthorhodamine compound. In one embodiment, the naphthofluorescein compound is selected from a seminaphthofluorescein compound and a carboxynaphthofluorescein compound. In one embodiment, the seminaphthofluorescein compound is selected from 5'(and 6')-carboxy-3,10-dihydroxy-spiro[7H-benzo[c]xanthene-7,1'(3'H)-isobenzofuran]-3'-one (also referred to herein as "SNAFL-1", see FIG. 7A) and 2-(2-chloro-3-hydroxy-9-carboxyethyl-10-oxo-10H-benzo[c]xanthen-7-yl)benzoic acid (also referred to herein as "EBIO-3", see FIG. 7E).

In one embodiment, the fluorescent species immobilized on a substrate comprises a conjugate of a fluorescent species and a macromolecule. In one embodiment, the macromolecule is an albumin. In one embodiment, the macromolecule is a serum albumin. In one embodiment, the macromolecule is a human serum albumin. In one embodiment, the macromolecule is a recombinant human serum albumin. In one embodiment, the fluorescent species immobilized on a substrate comprises a naphthofluorescein/serum albumin conjugate. In one embodiment, the fluorescent species immobilized on a substrate comprises a seminaphthofluorescein/human serum albumin conjugate.

As noted above, the method is suitable for measuring the pH of blood or blood products sealed in a vessel. In one embodiment, the fluorescent species immobilized on a substrate is introduced into a sealed vessel by a means that preserves the vessel's seal.

In another aspect of the invention, a system for measuring pH is provided. In one embodiment, the system includes (a) a light source for exciting a fluorescent species, wherein the fluorescent species has a first emission intensity at a first emission wavelength and a second emission intensity at a second emission wavelength;

(b) a first emission detector for measuring the first emission intensity;

(c) a second emission detector for measuring the second emission intensity;

(d) an excitation lightguide for transmitting excitation light from the light source to the fluorescent species, wherein the lightguide comprises a first terminus proximate to the light source and a second terminus distal to the light source;

(e) a first emission lightguide for transmitting emission from the fluorescent species to the first emission detector, wherein the lightguide comprises a first terminus proximate to the detector and a second terminus distal to the detector;

(f) a second emission lightguide for transmitting emission from the fluorescent species to the second emission detector, wherein the lightguide comprises a first terminus proximate to the detector and a second terminus distal to the detector;

(g) a probe housing the distal termini of the excitation lightguide, first emission lightguide, and second emission light guide; and (h) an assembly for receiving the probe, the assembly comprising:
  (i) a housing for receiving the probe, wherein the housing is adapted for receiving the probe at a first end and terminating with a window at the second end, the window being transparent to the excitation and the emission light,
  (ii) a tip member reversibly connectable to the housing's second end, wherein the tip member is adapted to receive liquid from a sample to be measured, and
  (iii) a fluorescent species immobilized on a substrate intermediate the tip member and the window, wherein the fluorescent species immobilized on the substrate is in liquid communication with the sample during the measurement, and wherein the window physically isolates the probe member from the fluorescent species immobilized on the substrate.

In one embodiment, the light source is a light-emitting diode.

In one embodiment, the first and second detectors are photodiodes.

In one embodiment, the excitation lightguide, the first emission lightguide, and the second emission lightguide are optical fibers.

In one embodiment, the housing comprises a tapered tube terminating with the window.

In one embodiment, the tip member comprises a spike for puncturing a sealed vessel.

The fluorescent species useful in the system include those noted above in regard to the method and described in further detail below. In one embodiment, the fluorescent species comprises a seminaphthofluorescein/human serum albumin conjugate.

In a further aspect, the invention provides an assembly useful for introducing a fluorescent species immobilized on a substrate into a sample. The assembly is particularly useful for introducing a fluorescent species immobilized on a substrate into a sample sealed in a vessel. In one embodiment, the assembly includes (a) a housing having a first open end and a second closed end, wherein the closed end comprises a window transparent to visible light;

(b) a tip member reversibly connectable to the housing closed end, wherein the tip member is adapted to expose the housing window; and (c) a fluorescent species immobilized on a substrate intermediate the housing window and tip member.

The tip member is adapted to expose the housing window. By exposing the housing window to the environment exterior to the tip member, the fluorescent species immobilized on the substrate intermediate the housing window and tip member is in liquid communication with the sample to be measured.

In one embodiment, the housing is tapered. In one embodiment, the tip member comprises a spike for puncturing a sealed vessel. The fluorescent species useful in the assembly include those noted above in regard to the method and described in further detail below. In one embodiment, the fluorescent species comprises a seminaphthofluorescein/human serum albumin conjugate.

In another aspect, the invention provides a blood bag or blood product bag that includes the assembly described above.

In a further aspect of the invention, an environment-sensitive fluorophore protein conjugate is provided. In one embodiment, the conjugate includes an environment-sensitive fluorophore covalently coupled to an albumin. In one embodiment, the environment-sensitive fluorophore is a pH-sensitive fluorophore, an oxygen-sensitive fluorophore, a nucleic acid-sensitive fluorophore, an ion-sensitive fluorophore, a glucose-sensitive fluorophore, a lipid-sensitive fluorophore, or an enzyme-sensitive fluorophore.

In one embodiment, the environment-sensitive fluorophore is a pH-sensitive fluorophore selected from a naphthofluorescein compound and a seminaphthorhodamine compound. In one embodiment, the naphthofluorescein compound is a seminaphthofluorescein compound or a carboxynaphthofluorescein compound. In one embodiment, the seminaphthofluorescein compound is 5'(and 6')-carboxy-3,10-dihydroxy-spiro[7H-benzo[c]xanthene-7,1'(3'H)-isobenzofuran]-3'-one or 2-(2-chloro-3-hydroxy-9-carboxyethyl-10-oxo-10H-benzo[c]xanthen-7-yl)benzoic acid.

In one embodiment, the albumin is a serum albumin. In one embodiment, the albumin is a human serum albumin. In one embodiment, the albumin is a recombinant human serum albumin.

In one embodiment, the environment-sensitive fluorophore is 2-(2-chloro-3-hydroxy-9-carboxyethyl-10-oxo-10H-benzo[c]xanthen-7-yl)benzoic acid and the albumin is human serum albumin.

It will be appreciated that the method and system of the invention described above can be modified to include a particular environment-sensitive fluorophores to provide methods and systems specific to the utility provided by the particular fluorophore.

In another aspect, the invention provides a substrate-immobilized fluorescent species. In one embodiment, the substrate-immobilized fluorescent species is a membrane-immobilized fluorescent species. In one embodiment, the membrane-immobilized fluorescent species is a conjugate of a naphthofluorescein compound and an albumin adhered to a membrane. In one embodiment, the membrane is a microporous membrane. In one embodiment, the membrane is a nitrocellulose membrane, a membrane of mixed esters of nitrocellulose and cellulose acetate, a polyethylene terephthalate membrane, a polycarbonate membrane, and a polyimide membrane.

In one embodiment, the naphthofluorescein compound is a seminaphthofluorescein compound or a carboxynaphthofluorescein compound. In one embodiment, the naphthofluorescein compound is 5'(and 6')-carboxy-3,10-dihydroxy-spiro[7H-benzo[c]xanthene-7,1'(3'H)-isobenzofuran]-3'-one or 2-(2-chloro-3-hydroxy-9-carboxyethyl-10-oxo-10H-benzo[c]xanthen-7-yl)benzoic acid.

In one embodiment, the albumin is a serum albumin. In one embodiment, the albumin is a human serum albumin. In one embodiment, the albumin is a recombinant human serum albumin.

In another aspect of the invention, a method for measuring carbon dioxide is provided. In one embodiment, the method includes the steps of:

(a) irradiating a fluorescent species immobilized on a substrate with excitation light emanating from a probe physically isolated from the fluorescent species immobilized on the substrate, wherein the fluorescent species immobilized on the substrate is in liquid communication with a solution having pH responsiveness to carbon dioxide present in a liquid sample, wherein the solution having pH responsiveness to carbon dioxide is in communication with the liquid sample through a selectively permeable membrane, wherein the excitation light has a wavelength sufficient to effect fluorescent emission from the fluorescent species, wherein the fluorescent species exhibits a first emission intensity at a first emission wavelength and a second emission intensity at a second emission wavelength, the ratio of the first and second emission intensities being dependent on pH;

(b) measuring the first and second emission intensities to determined the pH of the solution having pH responsiveness; and (c) correlating the pH of the solution having pH responsiveness to the carbon dioxide level in the sample.

In one embodiment, the probe is physically isolated from the fluorescent species immobilized on the substrate by a window transparent to the excitation light and the fluorescent emission. In one embodiment, the probe comprises one or more optical fibers.

In one embodiment, the sample comprises blood or a blood product. In one embodiment, the sample is contained within a sealed vessel. In one embodiment, the fluorescent species immobilized on a substrate is introduced into a sealed vessel by a means that preserves the vessel's seal.

The fluorescent species useful in the method include those noted above in regard to the method for measuring pH and described in further detail below. In one embodiment, the fluorescent species comprises a seminaphthofluorescein/human serum albumin conjugate.

In another aspect, the invention provides a system for measuring carbon dioxide. The system is useful for measuring the carbon dioxide level in a liquid sample. In one embodiment, the system includes:

(a) a light source for exciting a fluorescent species, wherein the fluorescent species has a first emission intensity at a first emission wavelength and a second emission intensity at a second emission wavelength;

(b) a first emission detector for measuring the first emission intensity;

(c) a second emission detector for measuring the second emission intensity;

(d) an excitation lightguide for transmitting excitation light from the light source to the fluorescent species, wherein the lightguide comprises a first terminus proximate to the light source and a second terminus distal to the light source;

(e) a first emission lightguide for transmitting emission from the fluorescent species to the first emission detector, wherein the lightguide comprises a first terminus proximate to the detector and a second terminus distal to the detector;

(f) a second emission lightguide for transmitting emission from the fluorescent species to the second emission detector, wherein the lightguide comprises a first terminus proximate to the detector and a second terminus distal to the detector;

(g) a probe housing the distal termini of the excitation lightguide, first emission lightguide, and second emission light guide; and (h) an assembly for receiving the probe, the assembly comprising:

(i) a housing for receiving the probe, wherein the housing is adapted for receiving the probe at a first end and terminating with a window at the second end, the window being transparent to the excitation and the emission light, (ii) a tip member reversibly connectable to the housing's second end, wherein the tip member comprises a chamber for receiving a solution having pH responsiveness to carbon dioxide present in a liquid sample, wherein the solution having pH responsiveness to carbon dioxide is in liquid communication with the liquid sample through a selectively permeable membrane, and (iii) a fluorescent species immobilized on a substrate intermediate the tip member and the window, wherein the fluorescent species immobilized on the substrate is in liquid communication with the solution having pH responsiveness to carbon dioxide during the measurement, and wherein the window physically isolates the probe member from the fluorescent species immobilized on the substrate.

In one embodiment, the light source is a light-emitting diode.

In one embodiment, the first and second detectors are photodiodes.

In one embodiment, the excitation lightguide, the first emission lightguide, and the second emission lightguide are optical fibers.

In one embodiment, the housing comprises a tapered tube terminating with the window.

In one embodiment, the selectively permeable membrane is permeable to carbon dioxide.

In one embodiment, the tip member comprises a spike for puncturing a sealed vessel.

The fluorescent species useful in the method include those noted above in regard to the method for measuring pH and described in further detail below. In one embodiment, the fluorescent species comprises a seminaphthofluorescein/human serum albumin conjugate.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a schematic illustration of a representative housing for excitation and emission light guides useful in the system of the invention;

FIG. 3 illustrates the relationship between the excitation/emission optical fiber housing and the sealed vessel port;

FIGS. 4A-4C illustrate a representative port assembly for introducing a substrate-immobilized fluorescent species into a sealed vessel, FIG. 4A illustrates the assembled port, FIG. 4B is an exploded view of the port assembly; and FIG. 4C is a plan view of tip;

FIG. 5A shows a sealed vessel in which substrate is introduced through process of puncture and reseal, FIG. 5B shows a sealed vessel incorporating substrate during vessel manufacture;

FIGS. 7A-E illustrate the structures of representative seminaphthofluorescein compounds useful in the method and system of the invention;

DETAILED DESCRIPTION OF THE INVENTION

Figure 1A:
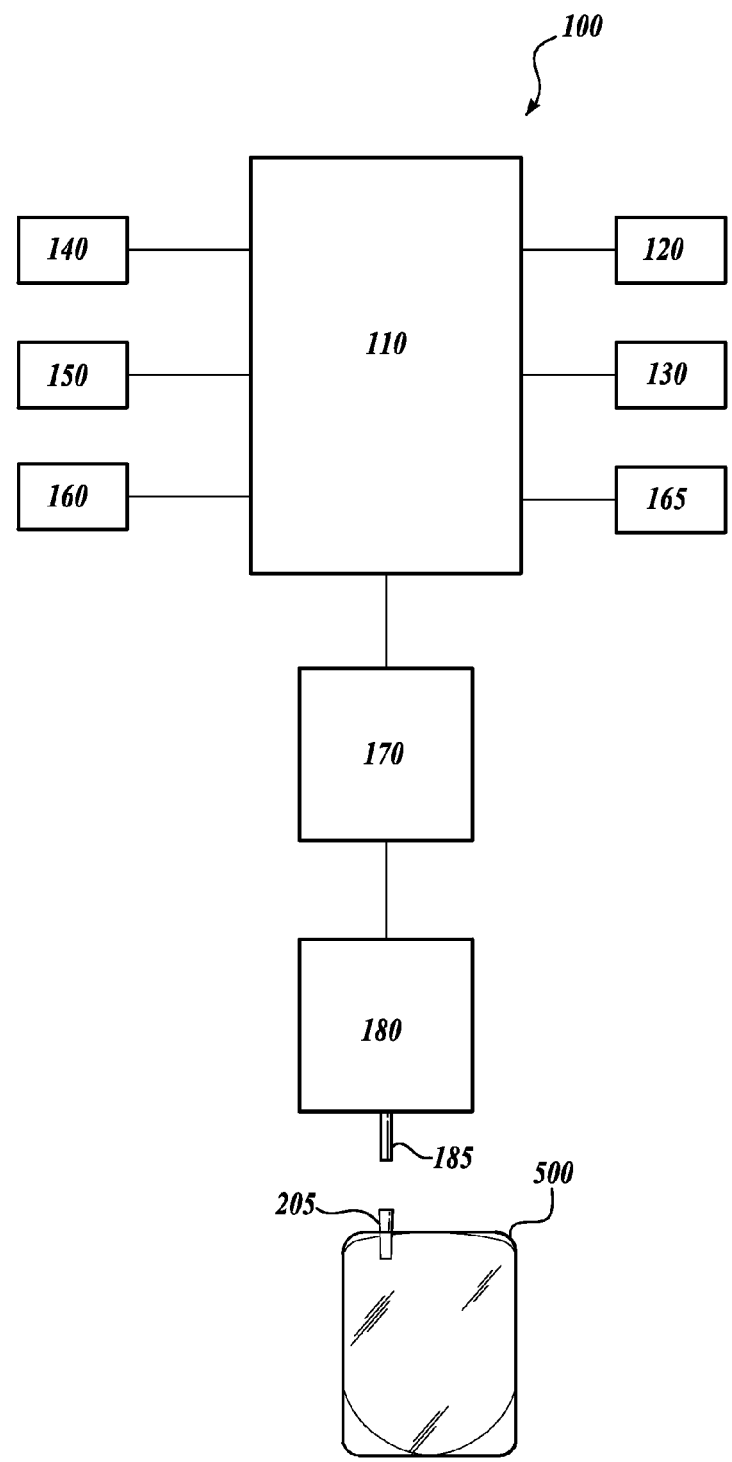
FIG. 1A is a schematic illustration of a representative system of the invention for measuring pH.

The present invention provides a method for measuring pH and a system for measuring pH. The method and system are suited to measure the pH of a specimen contained in a sealed container.

In one aspect of the invention, a method for measuring pH is provided. In the method, pH is determined by comparing fluorescent emission intensities from a single fluorescent species having pH-dependent fluorescent emission. The fluorescent species having pH-dependent fluorescent emission has a first emission intensity at a first wavelength and a second emission intensity at a second wavelength, the first and second emission intensities being characteristic of pH in the environment of the fluorescent species. The ratio of the first and second emission intensities provides pH measurement. Calibration of the first and second emission intensities provides an intensity-based reference (ratio information) that is used to determine the pH of the environment of the fluorescent species.

The method of the invention is a fluorescent wavelength-ratiometric method. As used herein, the term "fluorescent wavelength-ratiometric" refers to the method by which the first and second fluorescent emission intensities measured at first and second emission wavelengths, respectively, are ratioed to provide pH information.

In the method, the fluorescent species having pH-dependent fluorescent emission is immobilized on a substrate in contact with the sample such that the fluorescent species is in contact with the sample. The immobilized fluorescent species in contact with the sample is located in the sample such that the fluorescent species can be interrogated. The fluorescence measurement is made by irradiating the fluorescent species at a wavelength sufficient to elicit fluorescent emission, which is then measured. Because of the pH-dependent nature of the fluorescent species' emission profile (i.e., first and second fluorescent emission intensities measured at first and second emission wavelengths, respectively) the measurement of the fluorescent emission profile yields the pH of the fluorescent species' environment (i.e., sample pH).

In one embodiment of the method of the invention, the sample for which the pH is to be determined is contained in a sealed vessel. This method is suitable for measuring pH of blood and blood products sealed in a conventional blood storage vessel.

In another embodiment, the sample for which the pH is to be determined is contained in an open vessel. As used herein, the term "open vessel" refers to a vessel that is not sealed. This method is suitable where contamination of the sample being measured is to be avoided. In this method, the probe is cleaned and/or sterilized and is used once and discarded. This method is suitable for measuring the pH of materials used in food, pharmaceutical, or biological research where the vessel containing the material is not sealed (i.e., open). Such a "lab-use" system includes a tip (see description below) placed onto the probe. The pH measurement is made by immersing the tip into the sample and measuring pH. The tip is removed from the sample, removed from the probe, and discarded.

In the method for measuring the pH of a contained sample, the substrate-immobilized fluorescent species is introduced into the vessel either before or after the sample is placed in the vessel. As used herein, the term "sealed vessel" refers to a vessel that prevents its contents from exposure to the environment exterior to the vessel. The sealed vessel prevents the contents of the vessel from contact from, for example, liquids and gases outside of the vessel. The sealed vessel also prevents the contents of the vessel from escaping the vessel.

The vessel can be manufactured to include the substrate-immobilized fluorescent species as a component of the vessel. In such an embodiment, the substrate-immobilized fluorescent species is incorporated into the vessel during manufacture to provide a vessel into which a sample can be later introduced and its pH measured. The manufacture of a vessel incorporating the substrate-immobilized fluorescent species is described in Example 1.

Alternatively, the substrate-immobilized fluorescent species can be introduced into the vessel after the sample has been introduced into the vessel. In such an embodiment, the substrate-immobilized fluorescent species is introduced into the vessel by a process in which the vessel is first punctured (or spiked) to introduce the substrate-immobilized fluorescent species and then resealed to provide a sealed vessel including the sample now in contact with the substrate-immobilized fluorescent species. The process for introducing the substrate-immobilized fluorescent species into a sealed vessel is described in Example 2.

As noted above, the vessel including the substrate-immobilized fluorescent species in contact with the sample is sealed before, during, and after interrogation. Interrogation of the fluorescent species requires excitation of the species at a wavelength sufficient to effect fluorescent emission from the species and measurement of that fluorescent emission. In the method of the invention, interrogation is accomplished through a window in the sealed vessel. The fluorescent species is excited by irradiation through the window, and emission from the fluorescent species is collected from the fluorescent species though the window. The window is a component of the sealed vessel and allows for interrogation of the fluorescent species in contact with the sample. The window is sufficiently transparent at the excitation and emission wavelengths to permit interrogation by the method. The substrate-immobilized fluorescent species is positioned in proximity to the window sufficient for interrogation: proximity sufficient to effectively excite the fluorescent species and to effectively collect emission from the fluorescent species. It will be appreciated that for epifluorescence applications, a single window is used. However, other methods and devices of the invention can include other optical paths, such as straight-through or right angle optical paths, where more than one window can be used.

The method of the invention includes irradiating the substrate-immobilized fluorescent species, which in one embodiment is contained along with a sample in a sealed vessel, at a wavelength sufficient to effect emission from the fluorescent species and to measure that emission. Exciting light and fluorescent emission pass through the sealed vessel's window. In one embodiment, the sealed vessel further includes a port for receiving a housing that holds the excitation light guide and emission light guide. In one embodiment, the excitation light guide includes one or more optical fibers that transmit the excitation light from a light source to the fluorescent species. In one embodiment, the emission light guide includes one or more optical fibers that transmit the emission light from the fluorescent species to a light detector. The port receiving the housing is positioned in proximity to the window sufficient for interrogation: proximity sufficient to effectively excite the fluorescent species and to effectively collect emission from the fluorescent species.

As with all optical fluorescent methods, the method of the invention includes a light source for exciting the fluorescent species and a detector for measuring the emission of the fluorescent species. Light sources, wavelength selection filters, and detectors are selected based on the absorbance and emission profiles of the fluorescent species used in the method.

Suitable light sources provide excitation energy at a wavelength and intensity sufficient to effect fluorescent emission from the fluorescent species. The light source can provide relatively broad wavelength band excitation (e.g., ultraviolet or white light sources) or relatively narrower wavelength band excitation (e.g., laser or light-emitting diode). To enhance excitation efficiency and emission measurement, relatively broad wavelength band exciting light from the source can be selected and narrowed through the use of diffraction gratings, monochromators, or filters to suit the fluorescent species. Suitable light sources include tungsten lamps, halogen lamps, xenon lamps, arc lamps, LEDs, hollow cathode lamps, and lasers.

Suitable detectors detect the intensity of fluorescent emission over the emission wavelength band of the fluorescent species. To enhance emission measurement, fluorescent emission from the fluorescent species source can be selected and narrowed through the use of diffraction gratings, monochromators, or filters to suit the fluorescent species. Suitable detectors include photomultiplier tubes and solid state detectors, such as photodiodes, responsive to the wavelength emission band of the fluorescent species. Other suitable detectors are photovoltaic cells, PIN diodes, and avalanche photodiodes.

Through the use of filters, all of the excitation light that reflects off the target is filtered out before reaching the detector. This can be achieved by using filters in both the excitation and emission optical paths. In certain instances, reflected excitation light (which is many orders of magnitude more intense than the emission light) that reaches the detector can swamp the specific signal. Generally, 10E5 ($10^5$) or greater out-of-band rejection is appropriate in each of the filter sets. Reduction of excitation light can also be achieved by using an angled window so that reflected light is directed away from the emission detector. However, such an optical path is not as effective as filter sets.

Excitation light from the source can be directed to the fluorescent species through the use of a light guide, such as one or more optical fibers. Similarly, emission from the fluorescent species can be directed to the detector through the use of a light guide, such as one or more optical fibers.

A representative system for carrying out the method of the invention is illustrated schematically in FIG. 1A. Referring to FIG. 1A, system 100 includes controller 110 that controls and operates the system components. System components include keypad 120 for inputting information including system commands; display 130 for determining the status of the system and viewing pH determination results; barcode reader 140 for inputting information to the system including the identification of the sample, the pH of which is to be measured by the system; printer 150 for printing system status and pH determination results; battery (or wall plug and power adapter) 160 for powering the system; memory device 165 for storing test results and calibration data; signal processing electronics 170 for commanding the optical platform components and processing signals from the optical platform; and optical platform 180 including an excitation source, emission detectors, light guides, and associated lenses and filters. Optical platform includes probe member 185 housing one or more excitation light guides and two or more emission light guides. FIG. 1A also illustrates sealed vessel 500 including port 205 for receiving probe member 185.

Figure 1B:
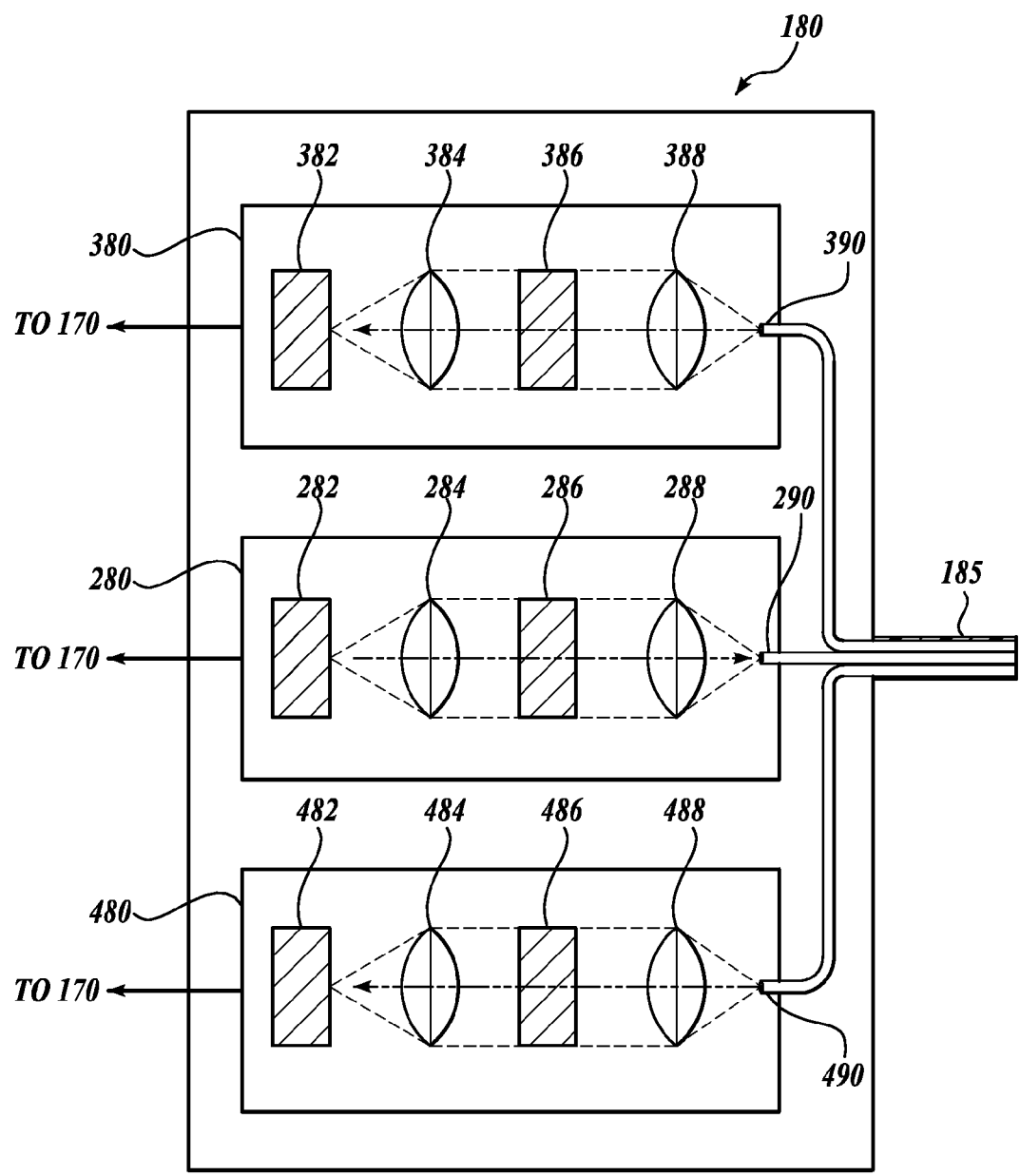
FIG. 1B is a schematic illustration of an optical platform useful in the system of the invention for measuring pH.

FIG. 1B is a schematic illustration of an optical platform useful in the system of the invention for measuring pH. Referring to FIG. 1B, optical platform 180 includes excitation optics 280, first emission optics 380, and second emission optics 480. Excitation optics 280 include light source 282, collimating lens 284, filter 286, focusing lens 288, and excitation light waveguide 290. First emission optics 380 include detector 382, focusing lens 384, filter 386, collimating lens 388, and first emission light waveguide 390. Second emission optics 480 includes detector 482, focusing lens 484, filter 486, collimating lens 488, and second emission light waveguide 490. Excitation light guide 290, first emission light waveguide 390, and second emission light waveguide 490 are housed in probe member 185.

The system's light source is effective in exciting the fluorescent species. Suitable light sources include light-emitting diodes, lasers, tungsten lamps, halogen lamps, xenon lamps, arc lamps, and hollow cathode lamps. In one embodiment, the light source is a light-emitting diode emitting light in the range from 500 to 560 nm. A representative light-emitting diode useful in the system of the invention is a green ultrabright Cotco 503 series LED commercially available from Marktech, Latham N.Y.

The collimating lens directs light (e.g., excitation light from the light source or first and second emission light from the emission light waveguides) to the bandpass filter. Suitable collimating lenses include Biconvex glass lenses and Plano-convex glass lenses. Representative collimating lenses useful in the system of the invention are the Tech Spec PCX lenses commercially available from Edmund Optics, Barrington, N.J. The excitation collimating lens is 12×36 (diameter by effective focal length in mm) and the first and second emission collimating lenses are 12×18.

The focusing lens focuses light from the bandpass filter to the excitation light waveguide or from the bandpass filter to the detector. Suitable focusing lenses include Biconvex glass lenses and Plano-convex glass lenses. Representative focusing lenses useful in the system of the invention are the Tech Spec PCX lenses commercially available from Edmund Optics, Barrington, N.J. The excitation focusing lens is 12×18 and the first and second emission focusing lenses are 12×15.

Filters are used in the optical platform to narrow the bandwidth of transmitted light.

Suitable excitation filters include bandpass filters, shortpass filters, longpass filters, or a combination of short and long pass filters. In one embodiment, the system uses a shortpass filter that passes light in the range from about 370 nm to 540 nm. A representative excitation shortpass filter useful in the system of the invention is 540ASP commercially available from Omega Optical, Brattleboro, Vt.

Suitable first emission filters include bandpass, shortpass, longpass, or a combination of short and longpass filters. In one embodiment, the bandpass filter passes light in the range from about 595 to 605 nm and has a full width at half height of 10 nm. A representative first emission bandpass filter useful in the system of the invention is 600DF10 commercially available from Omega Optical, Brattleboro, Vt.

Suitable second emission filters include bandpass, shortpass, longpass, or a combination of short and longpass filters. In one embodiment, the bandpass filter passes light in the range from about 562 to 573 nm and has a full width at half height of 10 nm. A representative second emission bandpass filter useful in the system of the invention is 568DF10 commercially available from Omega Optical, Brattleboro, Vt.

The excitation light waveguide transmits excitation light from the light source through the probe member to the fluorescent species. In one embodiment, the excitation light waveguide includes one or more optical fibers. In one embodiment, the excitation waveguide is a single optical fiber. A representative fiber optic useful in the system of invention is RO2-534 commercially available from Edmund Optics, Barrington, N.J.

The first and second emission light waveguides transmit fluorescent emission from the fluorescent species through the probe member to the first and second emission detectors, respectively.

In one embodiment, the first emission light waveguide includes one or more optical fibers. In one embodiment, the first emission light waveguide includes a plurality of optical fibers. In one embodiment, the first emission light waveguide includes four optical fibers. A representative fiber optic useful in the system of invention is RO2-533 commercially available from Edmund Optics, Barrington, N.J.

In one embodiment, the second emission light waveguide includes one or more optical fibers. In one embodiment, the second emission light waveguide includes a plurality of optical fibers. In one embodiment, the second emission light waveguide includes four optical fibers. A representative fiber optic useful in the system of invention is RO2-533 commercially available from Edmund Optics, Barrington, N.J.

Suitable optical fibers useful in the system of the invention include glass or plastic optical fibers from 0.2 to 2 mm diameter.

The system's first and second emission detectors are effective in measuring the first and second fluorescent emissions from the fluorescent species. Suitable detectors include photodiodes, PIN diodes, and photomultiplier tubes. In one embodiment, the first and second emission detectors are photodiodes responsive in the range from 400 to 800 nm. Representative photodiodes useful in the system of the invention include BPW34 commercially available from Vishay Intertechnology, Malvern, Pa.

A representative probe member housing excitation and emission light guides useful in the system of the invention is illustrated schematically in FIG. 2. As shown in FIG. 2, the light guides are optical fibers. Referring to FIG. 2, probe member 185 houses excitation light guide 290, a plurality of first emission light guides 390, and a plurality of second emission light guides 490. In the representative probe member shown in FIG. 2, there are four first emission light guides 390, and four second emission light guides 490. The four first emission light guides can be considered to be a first channel (e.g., measuring the first fluorescent emission from the fluorescent species) and the four second emission light guides can be considered to be a second channel (e.g., measuring the second fluorescent emission from the fluorescent species). In the illustrated representative probe member, the fibers from each of the two sets of fibers alternate (i.e., alternating fibers 390 and 490) around the central fiber (290). This configuration provides for evening out of "hot spots" so that light collected by the first set is similar to the light collected by the second set.

The relationship between the probe member housing the excitation/emission light guides and the sealed vessel port is illustrated schematically in FIG. 3. Referring to FIG. 3, probe member 185 is received by port 205. Port 205 includes window 210, which is transparent to excitation and emission wavelengths used in the fluorescent measurement. Excitation light emanating from light guide 290 passes through window 210 and interrogates substrate 220 on which the fluorescent species is immobilized and which, in the operation of the method of the invention, is in contact with the sample contained in sealed vessel 200. Irradiation of substrate 220 results in excitation of the substrate-immobilized fluorescent species and fluorescent emission from the fluorescent species. Emission from the fluorescent species is received by and transmitted through light guides 390 and 490 to detectors 382 and 482, respectively (see FIG. 1B). As noted above, the fluorescent species' first emission intensity and the second emission intensity will depend on the pH of the sample.

A representative port assembly for introducing the substrate-immobilized fluorescent species into a sealed vessel is illustrated in FIGS. 4A and 4B. FIG. 4A illustrates the assembled port and FIG. 4B is an exploded view of the port assembly.

Figure 21:
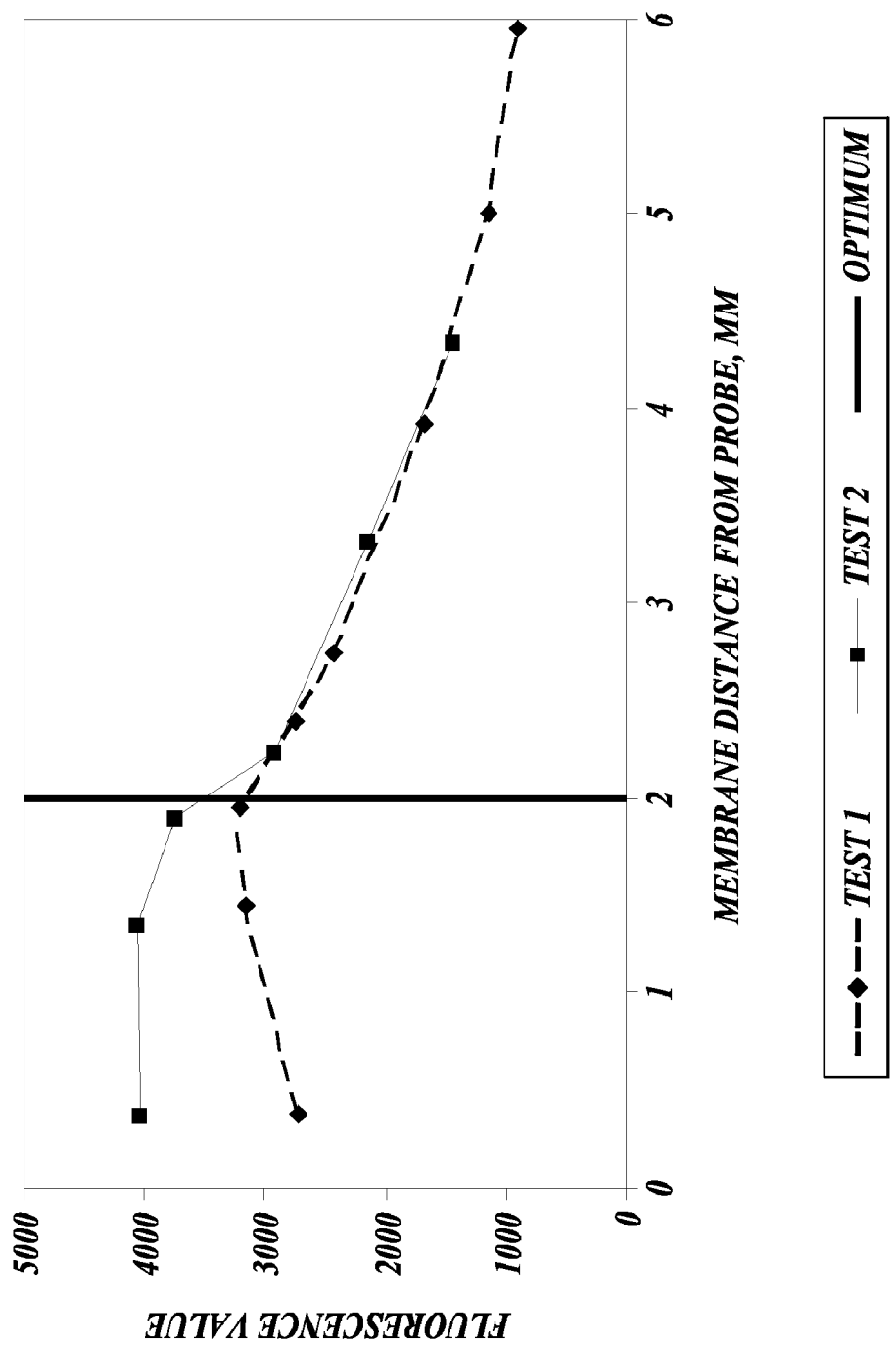
FIG. 21 illustrates the effect of probe position on fluorescent intensity in measuring pH in accordance with the invention.

Referring to FIGS. 4A and 4B, port assembly 202 includes port 205 and tip 215. Port 205 is a cylinder terminating with window 210 and having opening 212 for receiving probe member 185 (not shown). In one embodiment, port 205 tapers from opening 212 to window 210 such that the depth of insertion of probe member 185 into port 205 is predetermined by the probe's diameter. In one embodiment, the depth of travel of 185 in assembly 202 is limited by a ledge (not shown). In one embodiment, the optimal distance between probe and membrane was determined to be 2 mm or less. FIG. 21 illustrates the fluorescence intensity measured as a function of distance between the probe and membrane. When inserted in the port, the face of probe member 185 and window 210 are substantially parallel. Port 205 and tip 215 are adapted such that the port and tip are reversibly connectable. In one embodiment, port 205 includes annular inset 214 and tip 215 includes opening 216 defined by annular lip 218 for receiving inset 214. In this embodiment, inset 214 has a diameter less than opening 216. It will be appreciated that the connecting relationship between the port and tip can be reversed (i.e., port having annular lip for receiving tip having inset). Lip 218 defines bed 222 for receiving substrate 220, which is secured in port assembly 202 when port 205 is connected to tip 215. Tip 215 includes aperture 224 in bed 222. Aperture 224 provides for contact of substrate 220 with a liquid sample contained in a sealed vessel into which port assembly is introduced. Tip 215 terminates with apex 226 that facilitates the introduction of port assembly 202 into a sealed vessel by puncture. FIG. 4C is a plan view of tip 215 illustrating bed 222 and aperture 224. In one embodiment, the assembly is made from Lexan HPS1 1125 available from GE Polymerland, Pittsfield, Mass.

Figure 5A:
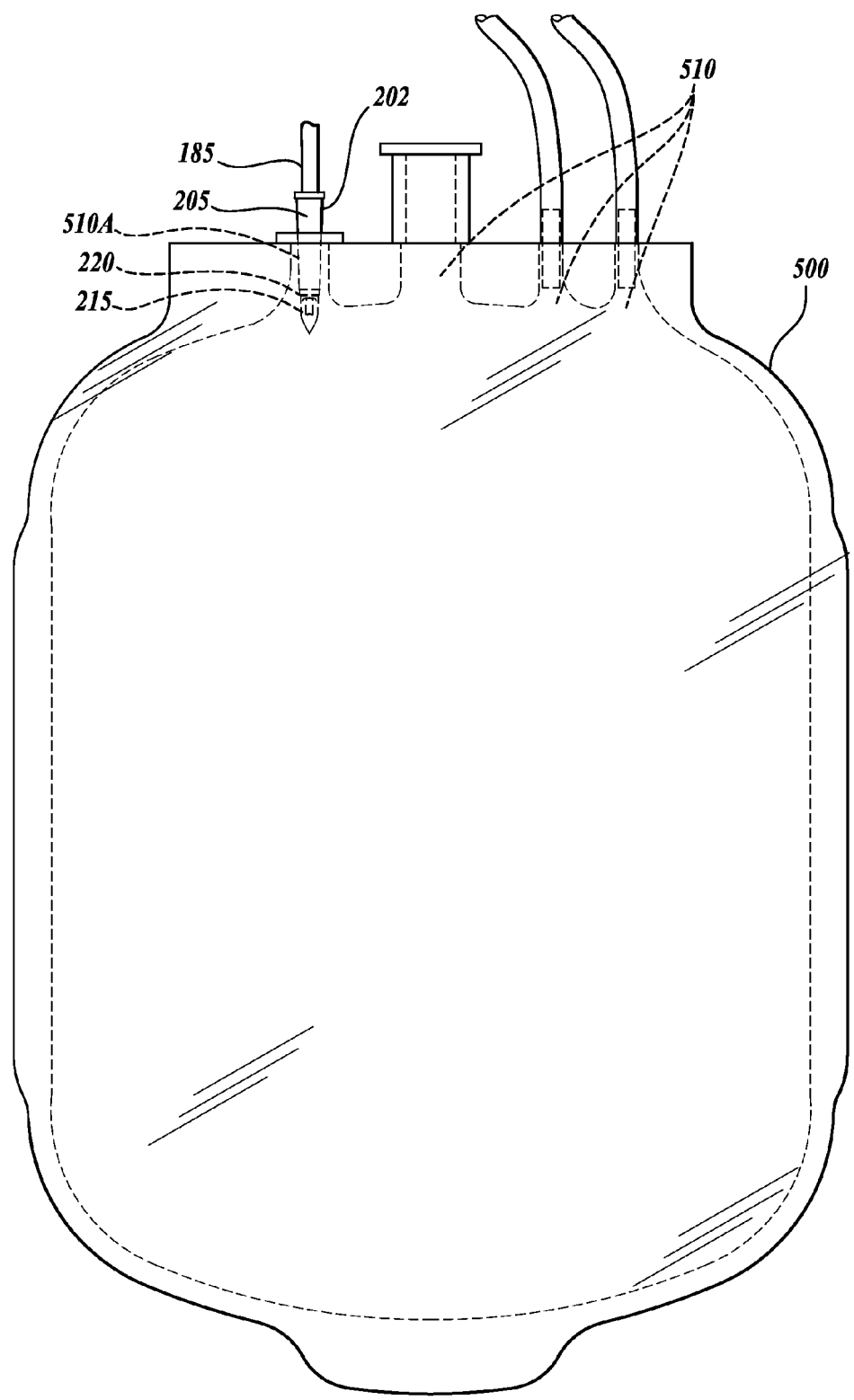
FIGS. 5A and 5B illustrate representative sealed vessels incorporating the substrate-immobilized fluorescent species.
Figure 5B:
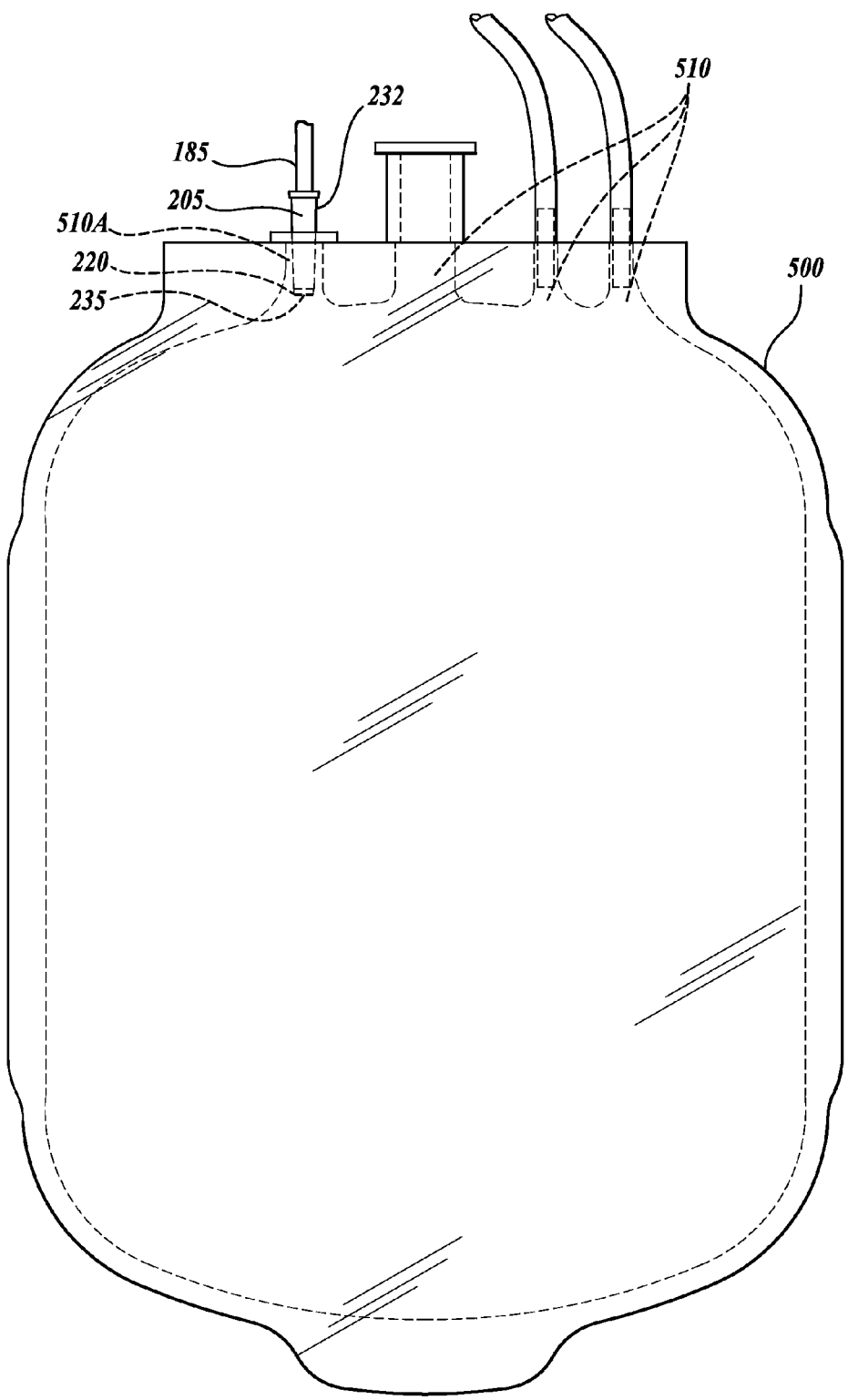

Representative sealed vessels incorporating the substrate-immobilized fluorescent species are illustrated in FIGS. 5A and 5B. FIG. 5A illustrates a sealed vessel into which a port assembly has been inserted by puncture. FIG. 5B illustrates a sealed vessel manufactured to include a port assembly.

Referring to FIG. 5A, sealed vessel 500 includes a plurality of vessel ports 510. Port assembly 202 (including port 205, membrane 220, and tip 215) resides in vessel port 510A after insertion. Vessel 500 remains sealed after insertion of port assembly 202. Vessel port 510A seals to port 205.

Referring to FIG. 5B, sealed vessel 500 includes a plurality of vessel ports 510. Port assembly 232 (including port 205, membrane 220, and tip 215) resides in vessel port 510A after vessel manufacture. A process for manufacturing a representative sealed vessel incorporating a port assembly is described in Example 1.

Figure 6:
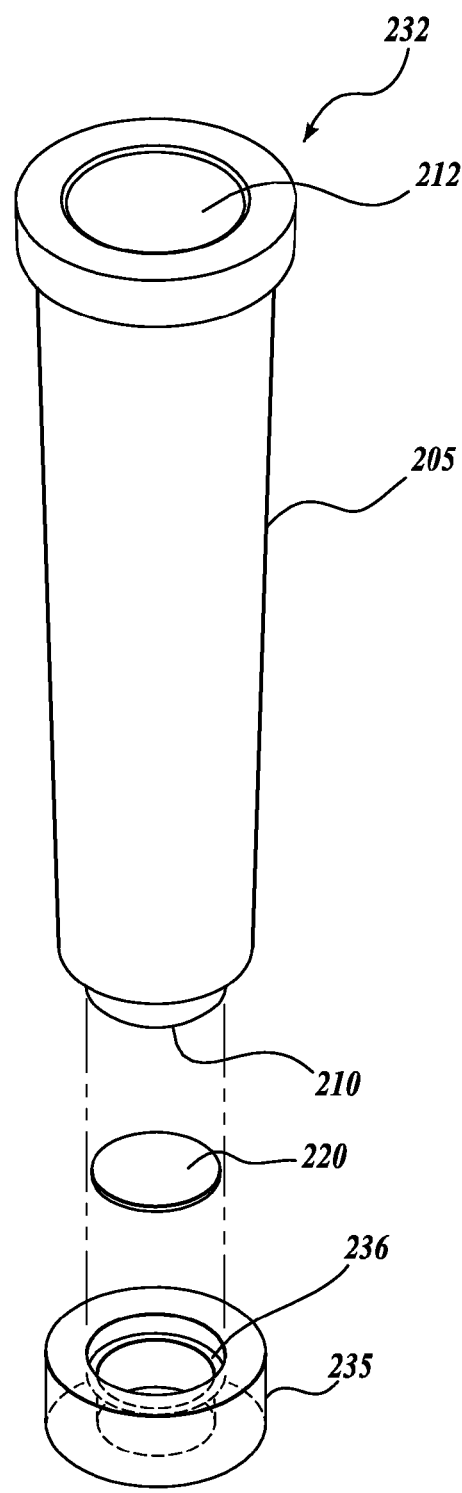
FIG. 6 is a representative port assembly useful in the manufacture of a sealed vessel.

A representative port assembly useful for incorporation into a sealed vessel during manufacture is illustrated in FIG. 6. The port assembly useful for incorporation during vessel manufacture is substantially the same as the port assembly useful for introduction into a sealed vessel illustrated in FIG. 4, except that the assembly useful in vessel manufacture need not include, and preferably does not include, a feature for puncturing the vessel. Referring to FIG. 6, port assembly 232 includes port 205 and tip 235. Port 205 is a cylinder terminating with window 210 and having opening 212 for receiving probe member 185 (not shown). In one embodiment, port 205 tapers from opening 212 to window 210 such that the depth of insertion of probe member 185 into port 205 is predetermined by the probe's diameter. When inserted in the port, the face of probe member 185 and window 210 are substantially parallel. Port 205 and tip 235 are adapted such that the port and tip are reversibly connectable. In one embodiment, port 205 includes annular inset 214 and tip 235 includes opening 216 defined by annular lip 218 for receiving inset 214. In this embodiment, inset 214 has a diameter less than opening 216. It will be appreciated that the connecting relationship between the port and tip can be reversed (i.e., port having annular lip for receiving tip having inset). Lip 218 defines bed 222 for receiving substrate 220, which is secured in port assembly 202 when port 205 is connected to tip 235. Tip 235 includes aperture 224 in bed 222. Aperture 224 provides for contact of substrate 220 with a liquid sample contained in the sealed vessel.

Fluorescent species having pH-dependent emission. The method and system of the invention for measuring pH uses a fluorescent species having pH-dependent fluorescent emission. The fluorescent species has a first emission intensity at a first wavelength and a second emission intensity at a second wavelength, the first and second emission intensities being characteristic of pH in the environment of the fluorescent species. The ratio of the first and second emission intensities provides pH measurement. It is appreciated that fluorescent emission occurs as a wavelength band having a band maximum that is referred to herein as the emission wavelength.

In one embodiment, the separation between the first wavelength and the second wavelength is at least about 40 nm. In one embodiment, the separation between the first wavelength and the second wavelength is at least about 30 nm. In one embodiment, the separation between the first wavelength and the second wavelength is at least about 20 nm. Using 10 nm HBW filters, the separation is at least about 30 nm. Preferably, the system of the invention achieve fluorescence signal separation by removing any emission band overlap by 10E5 or more.

The method and system of the invention for measuring pH are not limited to any particular fluorescent species, nor any particular pH range. The method and system of the invention is operable with any fluorescent species having pH-dependent properties that can be excited and its emission measured. The range of pH measurable by the method and system of the invention can be selected and is determined by the pH-dependent properties of the fluorescent species.

In addition to their pH-dependent properties noted above, suitable fluorescent species include those that can be substantially irreversibly immobilized on a substrate. The fluorescent species can be covalently coupled to the substrate or non-covalently associated with the substrate.

Suitable pH-dependent fluorescent species include those known in the art. Representative fluorescent species having suitable pH-dependent properties include fluorescein derivatives including naphthofluorescein compounds, seminaphthofluorescein compounds (e.g., SNAFL compounds), and seminaphthorhodafluor compounds (e.g., SNARF compounds). These compounds have advantages associated with their long wavelength emission, which is less susceptible to potential interfering light absorbing substances in blood. These compounds also have relatively long wavelength absorbance making them particularly suitable for excitation by commercially available LED light sources. Another compound having suitable pH dependent behavior is HPTS, 8-hydroxy-1,3,6-pyrenetrisulfonic acid. Although the compound has desired ratiometric pH properties, excitation is optimal at short wavelength (403 nm) where strong LED light sources are not commercially available. Representative SNAFL and SNARF compounds useful in the method and system of the invention are described in U.S. Pat. No. 4,945,171. Molecular Probes (now Invitrogen, Eugene, Oreg.) sells CNF, SNAFL, SNARF fluors with conjugatable carboxylic acid linker groups, see, for example, Molecular Probes Handbook (Ninth Edition) by R. P. Haugland, Chapter 21 "pH indicators" pages 829-847. Epoch Biosciences (now Nanogen, Bothell, Wash.) sells EBIO-3 with a propanoic acid linker. Whitaker et al. (Anal. Biochem. (1991) 194, 330-344) showed the synthesis of a number of SNAFL compounds. Wolfbeis et al. (Mikrochim Acta (1992) 108, 133-141) described the use of CNF and aminocellulose conjugates. The earliest reference to the SNAFL family of compounds is Whitaker et al. (1988) Biophys. J. 53, 197a. A related dye in the CNF family is VITA-BLUE, a sulfonenaphthofluorescein derivative (Lee et al (1989) Cytometry 10, 151-164) having a pKa of 7.56. A CNF analog with bromine substituents at each carbon adjacent to a phenol (pKa 7.45) has a pKa that is 0.54 pKa units lower than their measured pKa for CNF (pKa 7.99). Lee et al. note that "true" pKa values are difficult to determine for these compounds. A method for pKa determination is described in Example 3. SNAFL-1 (literature pKa~7.8) free acid had a pKa of 7.6 in that fluorescence-based assay.

The structures of seminaphthofluorescein compounds (SNAFL-1 and EBIO-3) useful in the method and system of the invention are illustrated below.

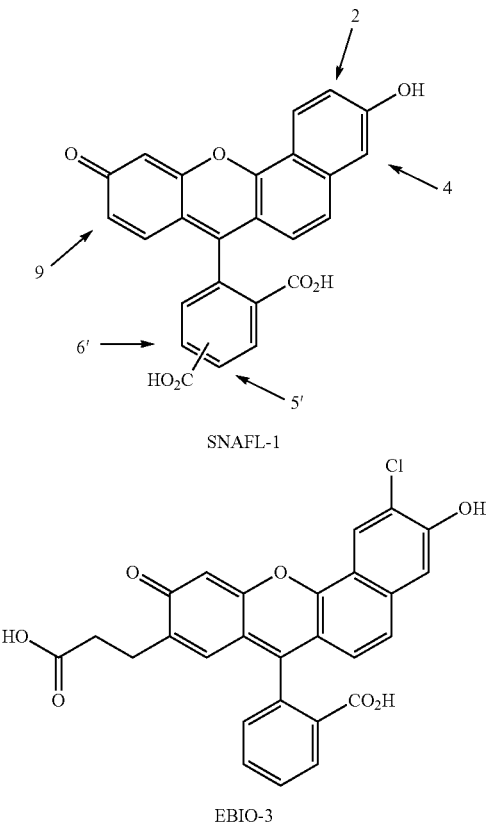

The numbering scheme describes position of attachment of linker molecules. These compounds have carboxylate linking groups suitable for conjugation to carrier proteins, as described below. For conjugation, the reactive N-hydroxysucinimide (NHS) ester of SNAFL-1 (commercially available from Molecule Probes, Inc., Eugene, Oreg.) can be used. Conjugation to lysine residues in human serum albumin (HSA) gave desired SNAFL/HSA conjugates. Carbodiimide activation of EBIO-3 gave a reactive intermediate that was efficiently conjugated to human serum albumin.

Representative naphthofluorescein and seminaphthofluorescein compounds useful in the method and system of the invention are illustrated in FIG. 7.

The SNAFL compounds are commercially available from Molecular Probes, Inc., Eugene, Oreg. The SNAFL compounds can be readily synthesized according to general procedures that have been published (see, for example, U.S. Pat. No. 4,945,171).

The preparation of a representative 2-chloro substituted SNAFL compound is shown below.

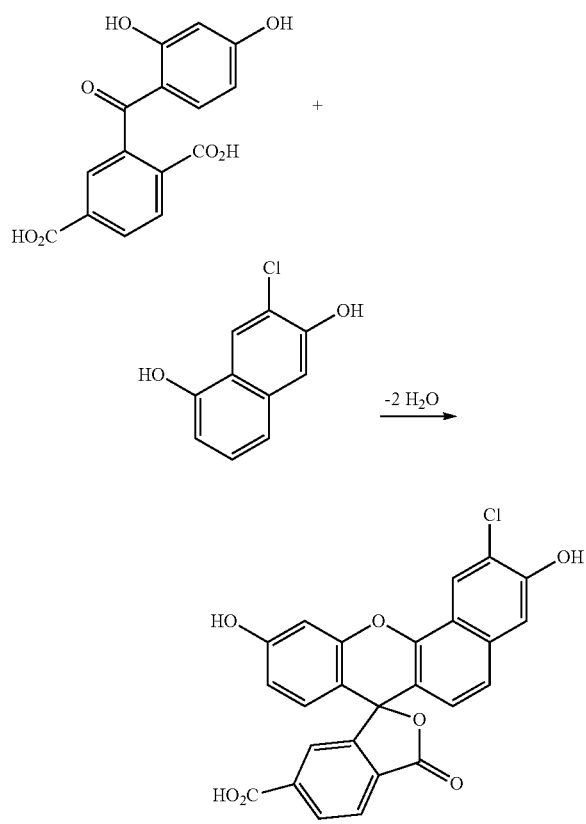

The compound can be prepared by condensation of 1,6-dihydroxynaphthalene with the diacid substituted 4-acylresorcinol in the presence of a dehydrating acid or Lewis acid catalyst, such as Zinc chloride.

The preparation of SNAFL compounds having propionic acid linkers is described in U.S. patent application Ser. No. 11/022,039, incorporated herein by reference in its entirety. A representative SNAFL compounds having a propionic acid linker, EBIO-3, is commercially available from Nanogen, Bothell Wash.

Figure 8:
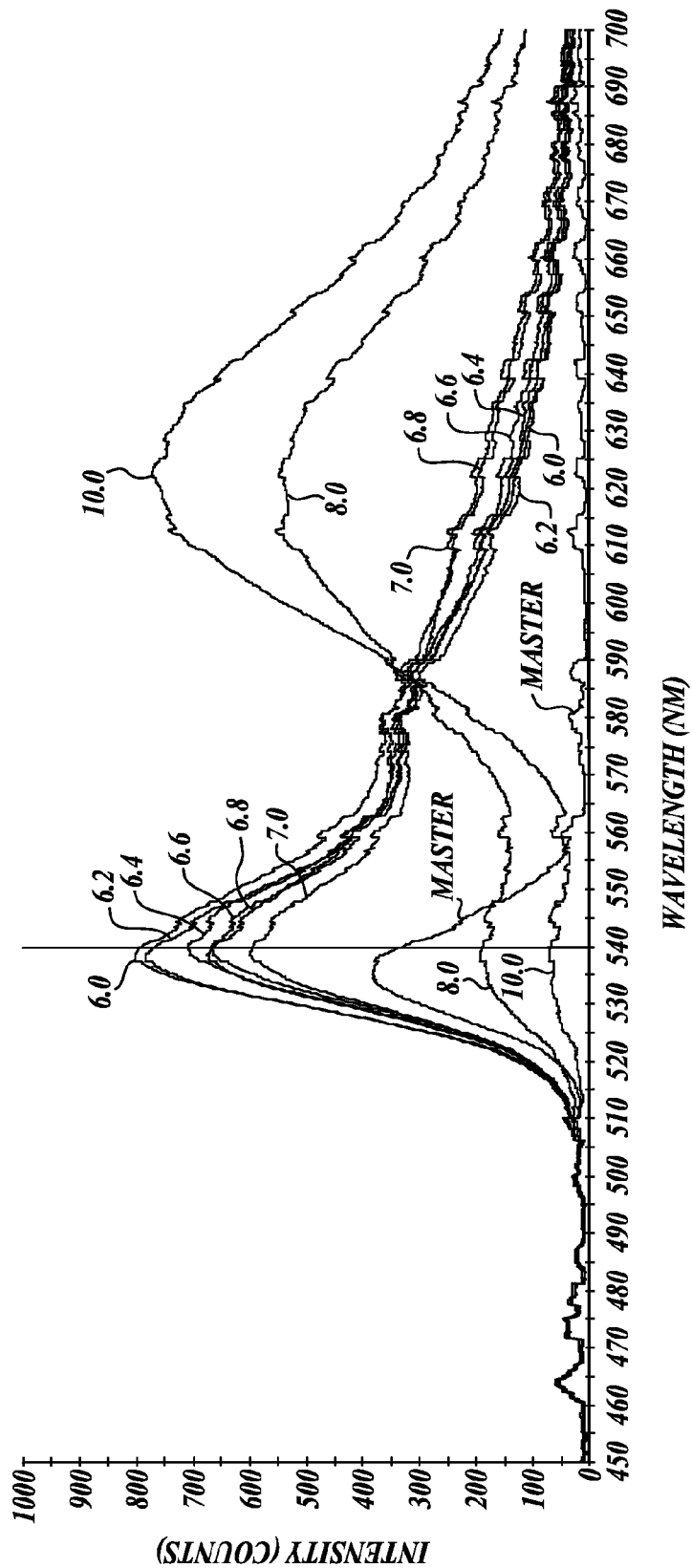
FIG. 8 illustrates the emission spectra as a function of pH of a representative fluorescent species (SNAFL-1) useful in the method and system of the invention.
Figure 9:
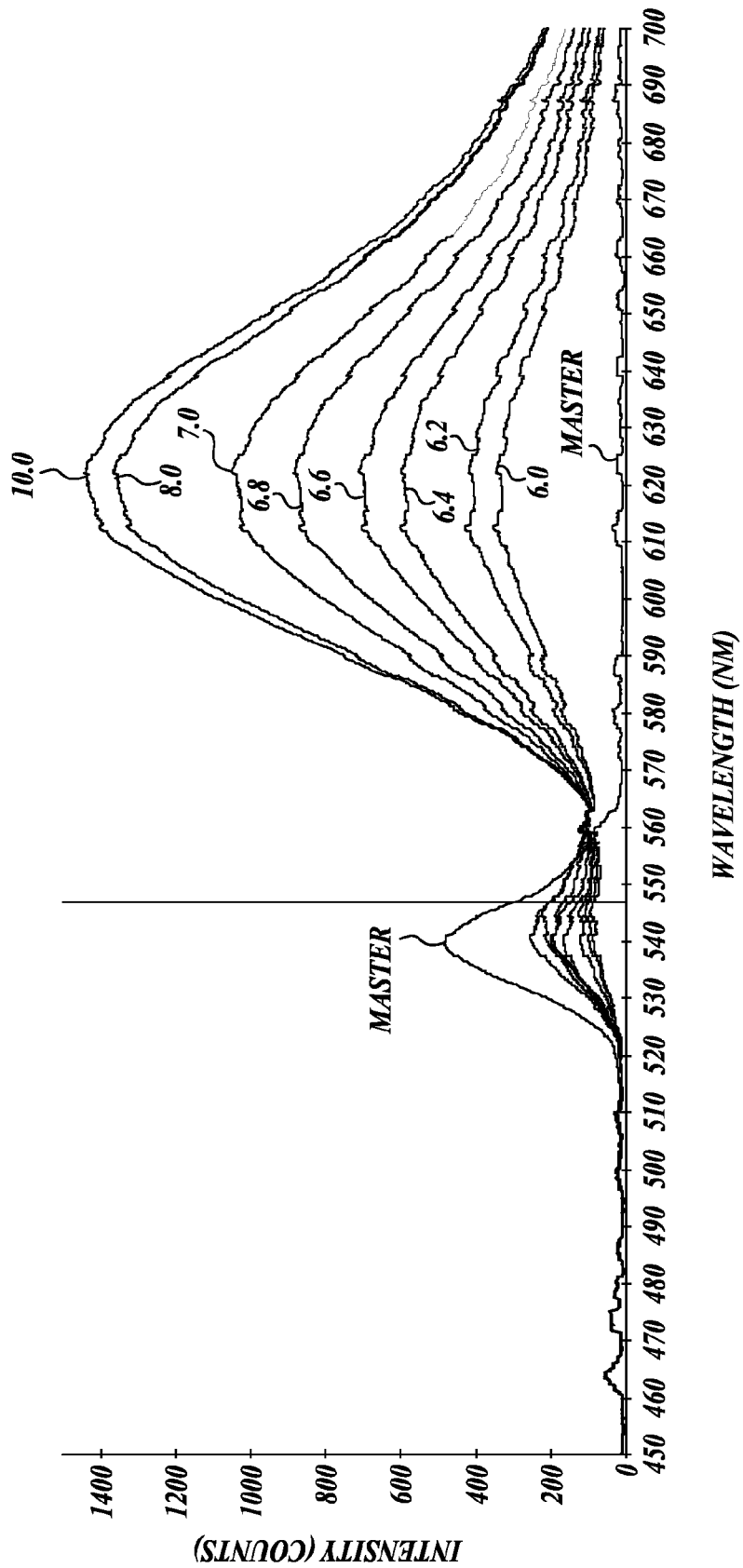
FIG. 9 illustrates the emission spectra as a function of pH of a representative fluorescent species (EBIO-3) useful in the method and system of the invention.

The emission spectra as a function of pH of representative fluorescent species (i.e., SNAFL-1 and EBIO-1) useful in the method and system of the invention are illustrated in FIGS. 8 and 9, respectively. FIG. 8 illustrates the emission spectra of SNAFL-1 in 50 mM potassium phosphate buffer as a function of pH (pH 6.0 to 10.0) (excitation at 540 nm). Referring to FIG. 8, the response at pH 6-7 is relatively poor (pKa=7.6). FIG. 9 illustrates the emission spectra of EBIO-3 in 50 mM potassium phosphate buffer as a function of pH (pH 6.0 to 10.0) (excitation at 545 nm). Referring to FIG. 9, the response at pH 6-7 is relatively good (pKa=6.6). Spectral properties and pKa data for the SNAFL analogs illustrated in FIGS. 7A-7E are summarized in Table 1.

TABLE 1 pH-Sensitive absorbance and emission of SNAFL analogs.

| Compound | Absorbance λmax (acid) | Absorbance λmax (base) | Emission λiso | Emission λmax (base) | pKa |
|---|---|---|---|---|---|
| SNAFL-1 | 482, 510 nm | 540 nm | 585 nm | 620 nm | 7.6 |
| SNAFL-2 | 485, 514 | 547 | 590 | 630 | 7.6 |
| EBIO-1 | 496, 519 | 545 | 560 | 620 | 6.5 |
| EBIO-2 | 506, 538 | 572 | 590 | 645 | 7.8 |
| EBIO-3 | 480, 509 | 534 | 560 | 610 | 6.6 |

Referring to Table 1, absorbance and emission spectra were obtained at 10 μM SNFL analog. Absorbance was measured at pH 6, 8, and 10: acid (pH 6) gave two bands of similar absorbance; pH 10 gave a single λmax (base). The emission spectra were determined by excitation at the absorbance λmax (base). The wavelength where emission spectra crossed is reported as λiso. The emission λmax was measured at pH 10. pKa was determined from fluorescence emission spectra. EBIO-1 and EBIO-3 were more sensitive to changes at pH~6.5. The other analogs were more sensitive at pH~8.

Fluorescent species conjugates for substrate immobilization. For use in the method and system of the invention, the fluorescent species is immobilized on a substrate such that the fluorescent species is in contact with the sample, the pH of which is to be measured. The fluorescent species can be immobilized on the substrate through the use of a material (e.g., macromolecular spacer material) having a strong associative interaction with the substrate. The spacer material allows covalent conjugation of the fluorescent species and provides large surface area needed for efficient non-covalent immobilization to the substrate surface. In one embodiment, the spacer material is human serum albumin (HSA) having ~44 lysine residues available for covalent conjugation. HSA's densely charged molecular structure has a passivating effect when adsorbed to biomaterials. Other advantages include reduced fluorescence quenching, uniform environment for the conjugated fluorophore, and availability in recombinant form (from yeast) so there is no chance of infection (as with HSA from donors). HSA conjugates are easily purified by ultrafiltration methods and form stable solutions that are easily characterized by absorbance and fluorescence assays to determine the number of fluorophores per protein.

In one embodiment, the fluorescent species is immobilized on the substrate through the use of a protein or protein fragment. Suitable proteins include those that can be substantially irreversibly immobilized on the substrate. The protein can be covalently coupled to the substrate or non-covalently associated with the substrate. Suitable proteins include proteins to which the fluorescent species can be substantially irreversibly immobilized. The fluorescent species can be covalently or non-covalently associated with the protein.

Suitable proteins include human serum albumin (HSA), bovine serum albumin (BSA), vonWillebrand's factor, kininogen, fibrinogen, and hemoglobin (no iron). Suitable proteins include proteins having available lysine residues (for conjugation to the fluorophore) and molecular weight sufficient to allow for immobilization efficiency to the blot membrane. Other functional groups in the protein (like cysteine) could presumably be used for covalent bonding to suitably reactive solid supports.

In one embodiment, the fluorescent species is immobilized on the substrate through the use of a polysaccharide. Suitable polysaccharides include those that can be substantially irreversibly immobilized on the substrate. The polysaccharide can be covalently coupled to the substrate or non-covalently associated with the substrate. Suitable polysaccharides include proteins to which the fluorescent species can be substantially irreversibly immobilized. The fluorescent species can be covalently or non-covalently associated with the polysaccharide.

Suitable polysaccharides include dextrans, aminodextrans, heparin, and lectins.

In another embodiment, the fluorescent species is immobilized on the substrate through the use of dendrimeric structures. Suitable dendrimeric structures include those that can be substantially irreversibly immobilized on the substrate. The dendrimeric structures can be covalently coupled to the substrate or non-covalently associated with the substrate. PAMAM dendrimers are commercially available as are other structural types and sizes.

In one embodiment, the fluorescent species is covalently coupled to a protein to provide a fluorophore-protein conjugate that can be immobilized on a substrate. In one embodiment, the fluorophore-polysaccharide conjugate is non-covalently associated with the substrate.

Figure 10:
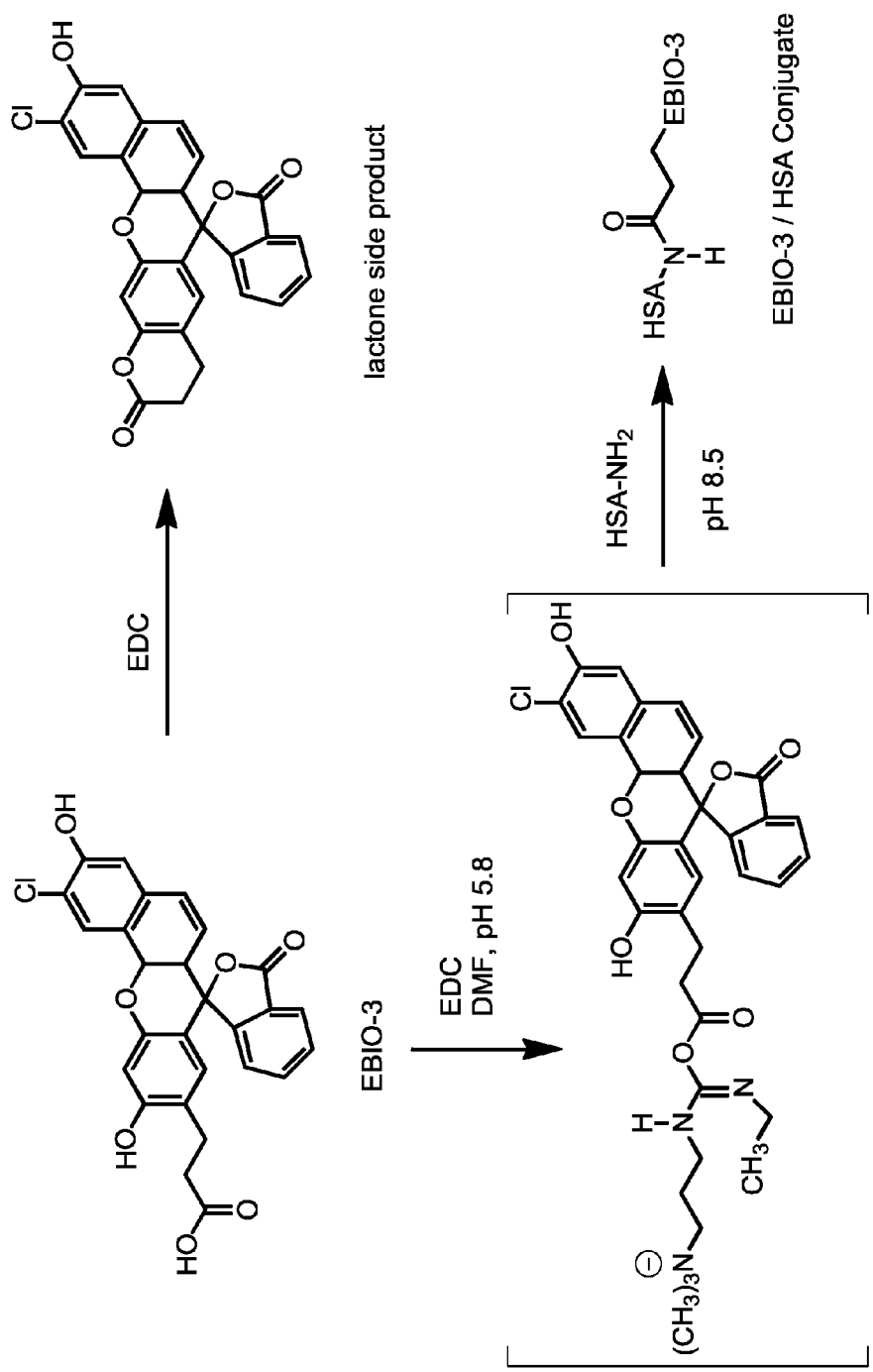
FIG. 10 is a schematic illustration of the preparation of a representative fluorophore-protein (EBIO-3/HSA) conjugate useful in the method and system of the invention.

In one embodiment, a fluorophore-protein conjugate is immobilized on a substrate. In one embodiment, the fluorescent species is a seminaphthofluorescein and the protein is human serum albumin. In one embodiment, the seminaphthofluorescein is SNAFL-1. The preparation of SNAFL-1/HSA conjugates is described in Example 4. The fluorescent properties of SNAFL-1/HSA conjugates are described in Example 5. In one embodiment, the seminaphthofluorescein is EBIO-3. The preparation of EBIO-3/HSA conjugates is described in Example 6. A schematic illustration of the coupling of EBIO-3 to HSA is illustrated in FIG. 10. The fluorescent properties of EBIO-3/HSA conjugates are described in Example 7.

Figure 11:
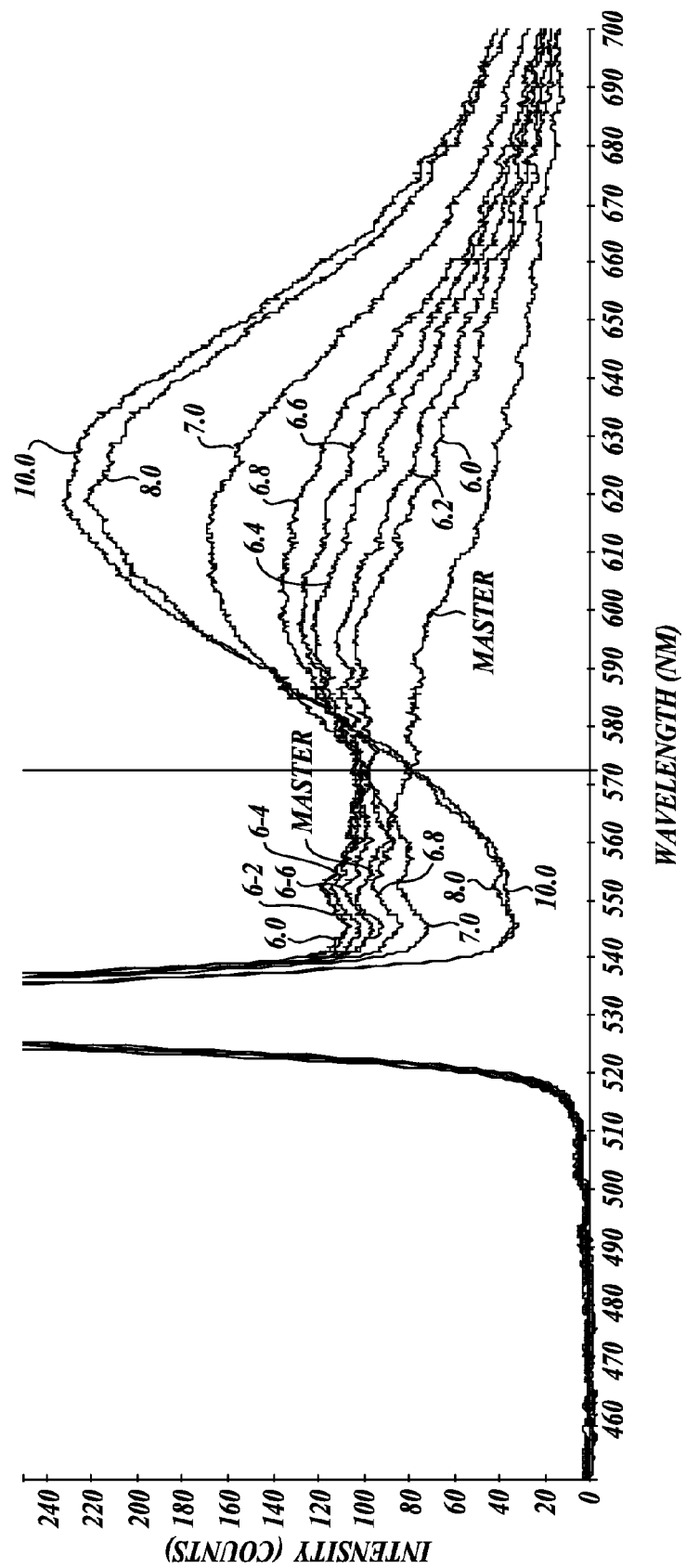
FIG. 11 illustrates the emission spectra as a function of pH of a representative fluorophore-protein conjugate (SNAFL-1/HSA) useful in the method and system of the invention.

The fluorescent emission spectra as a function of pH (6.0 to 10.0) of a representative fluorophore-protein conjugate (SNAFL-1/HSA, 1.6 fluorophores per HSA) useful in the method and system of the invention are illustrated in FIG. 11.

Figure 12:
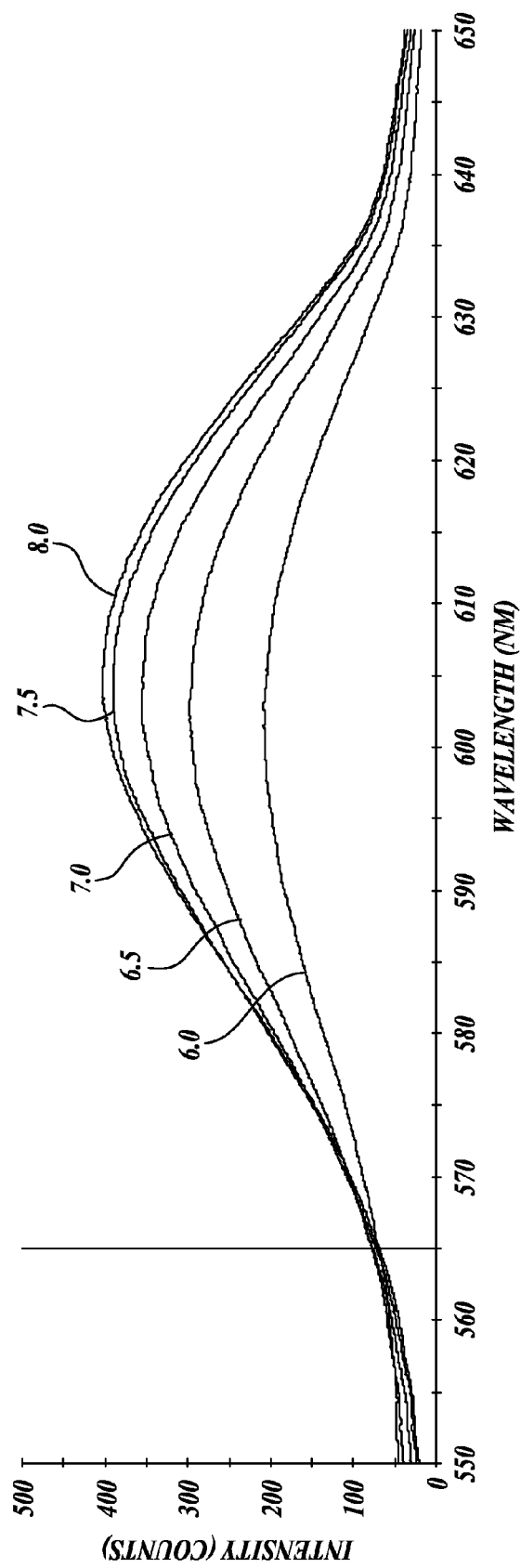
FIG. 12 illustrates the emission spectra as a function of pH of a representative fluorophore-protein conjugate (EBIO-3/HSA) useful in the method and system of the invention.

The fluorescent emission spectra as a function of pH (6.0 to 10.0) of a representative fluorophore-protein conjugate (EBIO-3/HSA, 1.92 fluorophores per HSA) useful in the method and system of the invention are illustrated in FIG. 12.

For the fluorophore-protein conjugate, the optimum fluorophore loading will vary depending on the particular fluorophore.

For SNAFL-1/HSA conjugates the fluorophore loading can vary from about 0.01 to about 40 SNAFL-1/HSA. Low signal at 0.01 and fluorescent quenching at 40 fluorophores/HSA. In one embodiment, the SNAFL-1 conjugate includes about 2 SNAFL-1/HSA.

For EBIO-3/HSA conjugates the fluorophore loading can vary from about 0.01 to about 40 EBIO-3/HSA. In one embodiment, the EBIO-3 conjugate includes about 2 EBIO-3/HSA.

Substrates for fluorescent species immobilization. In the method and system of the invention, the fluorescent species is immobilized on a substrate. As noted above, the fluorescent species can be directly immobilized on the substrate covalently or by non-covalent association or, alternatively, through the use of a material (e.g., fluorophore-protein conjugate) that can be immobilized on the substrate covalently or by non-covalent association.

Suitable substrates substantially irreversible immobilized the fluorescent species. In the method of the invention, suitable substrates also do not inhibit the contact of the liquid sample with the fluorescent species and do not impair or alter the pH measurement.

Figure 22:
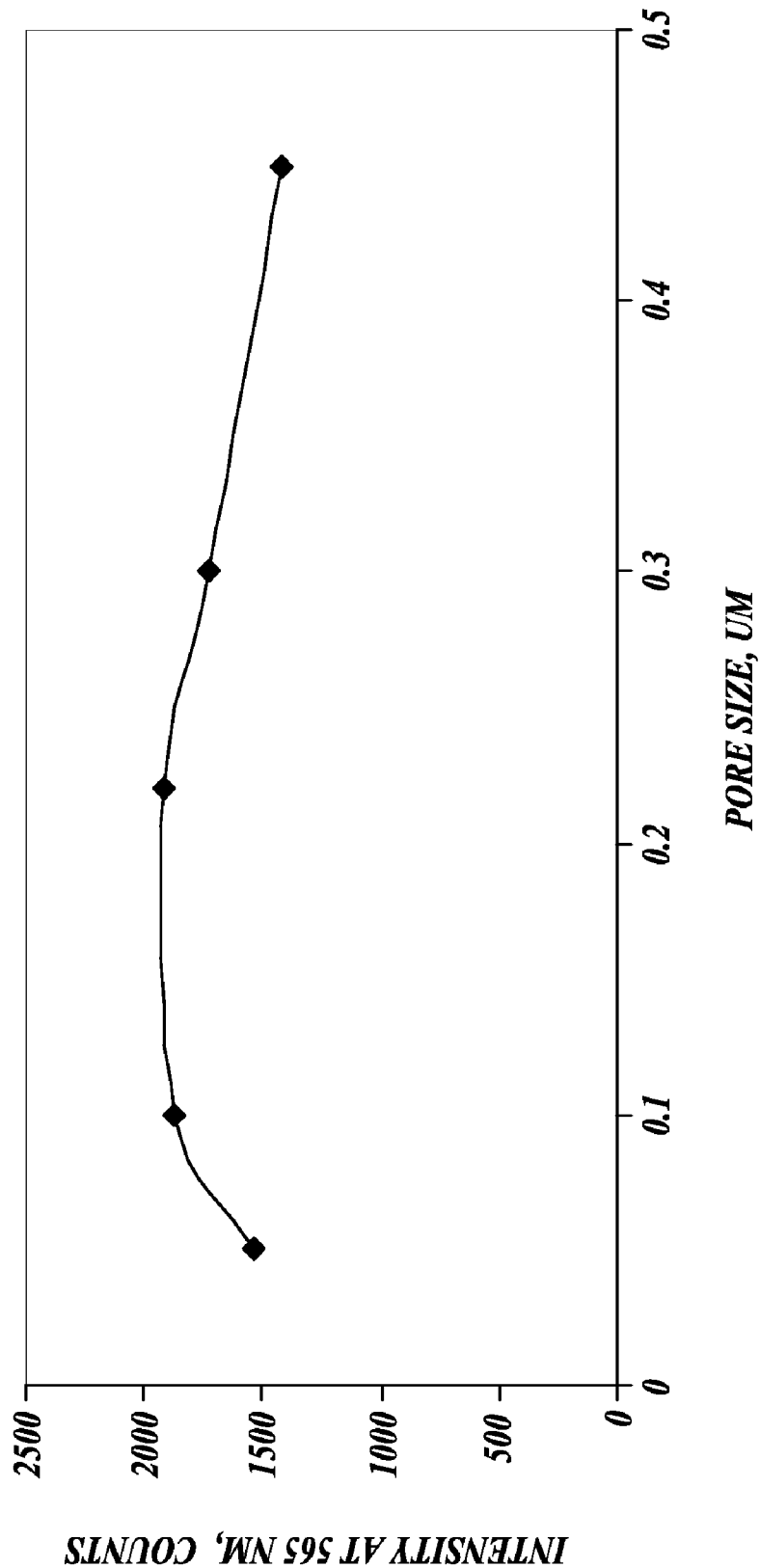
FIG. 22 illustrates the effect of membrane pore size on fluorescent intensity in measuring pH in accordance with the invention.

Representative substrates include membranes, such as microporous membranes made of nitrocellulose, mixed esters of nitrocellulose and cellulose acetate, polyethylene terephthalate, polycarbonate, polyvinylidene fluoride and polyimide. Such materials are available commercially from Whatman S&S, Florham Park, N.J. and Millipore, Billerica Mass. Suitable membranes include membranes in which the microporous structure is created by ion beam penetration such as membranes commercially available from Oxyphen Gmbh, Dresden, Germany under the designation OXYPHEN. Charged nylon surfaces (Nytran) can also be used. Suitable membranes include plastic membranes in which the microporous structure is made by injection molding the micropores into the plastic such as the processes used by Åmic, Stockholm, Sweden. Emission intensity of SNAFL-1/HSA at pH 7 immobilized on various pore size mixed ester nitrocellulose cellulose acetate membranes is shown in FIG. 22.

Immobilization of representative fluorophore protein conjugates on membranes is described in Examples 8 and 10. Example 8 describes the immobilization of SNAFL-1/HSA conjugates. Example 9 describes the fluorescent properties of immobilized SNAFL-1/HSA conjugates. Example 10 describes the immobilization of EBIO-3/HSA conjugates. Example 11 describes the fluorescent properties of immobilized EBIO-3/HSA conjugates.

Figure 13:
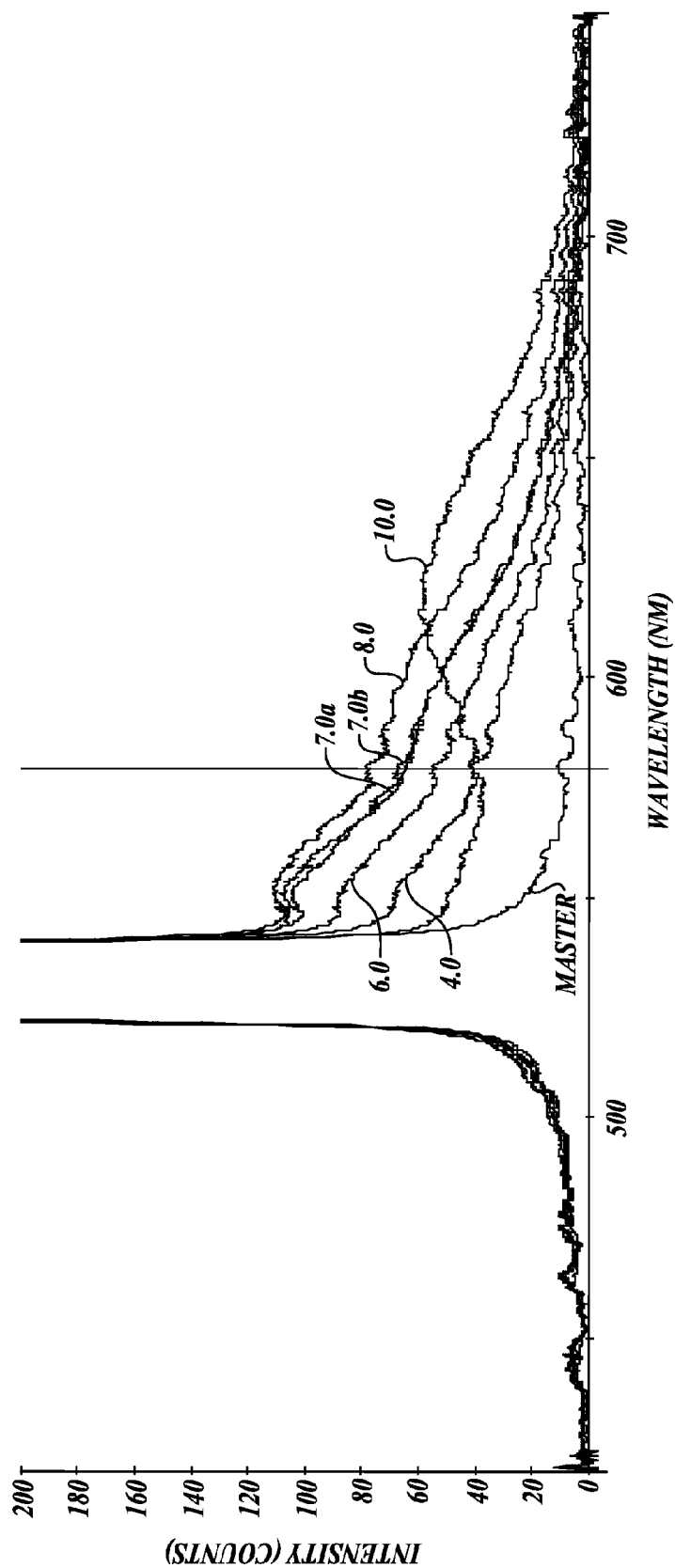
FIG. 13 illustrates the emission spectra of a representative substrate-immobilized fluorophore-protein conjugate (SNAFL-1/HSA) as a function of pH (Oxyphen)
Figure 14:
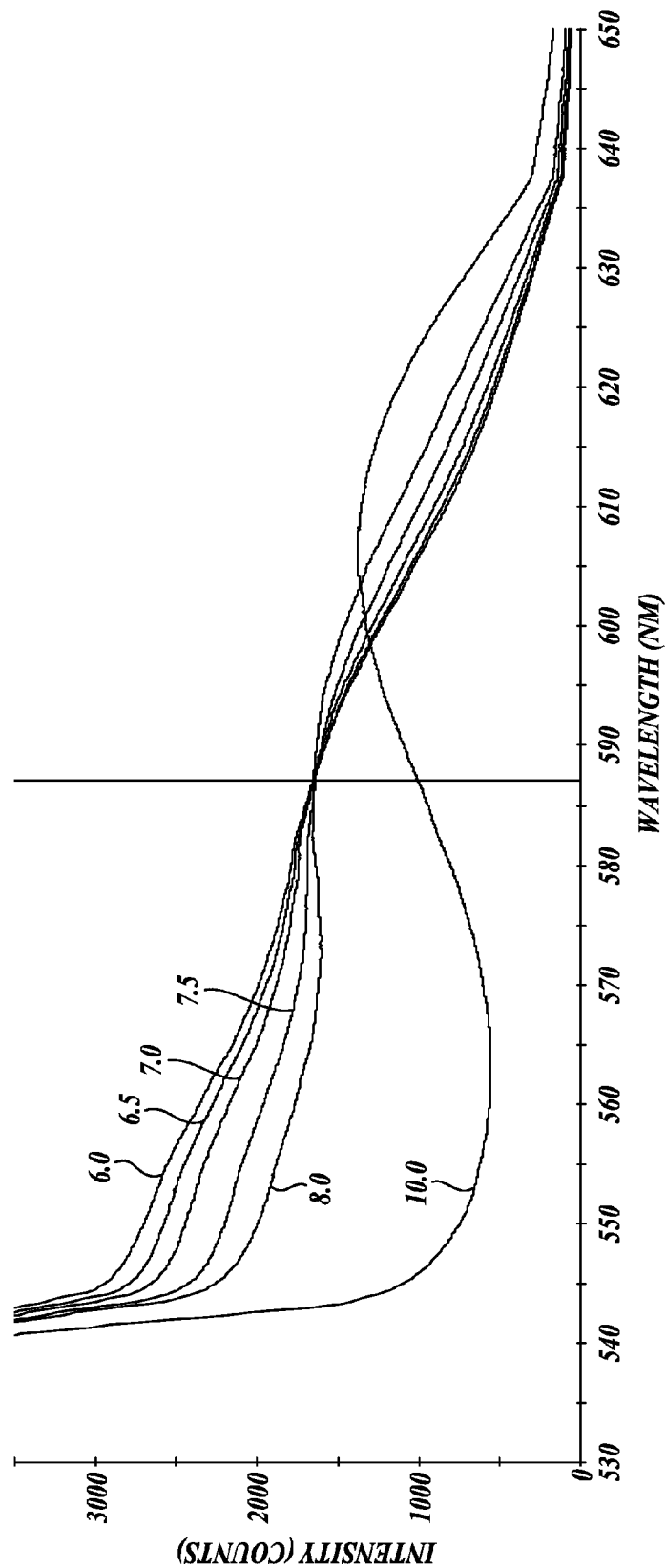
FIG. 14 illustrates the emission spectra of a representative substrate-immobilized fluorophore-protein conjugate (SNAFL-1/HSA) as a function of pH (nitrocellulose)

The emission spectra of a representative fluorophore-protein conjugate (SNAFL-1/HSA, 3.6:1) immobilized on Oxyphen and nitrocellulose as a function of pH (pH response), as measured by the microwell assay described in Example 9, are illustrated in FIGS. 13 and 14, respectively.

Figure 15:
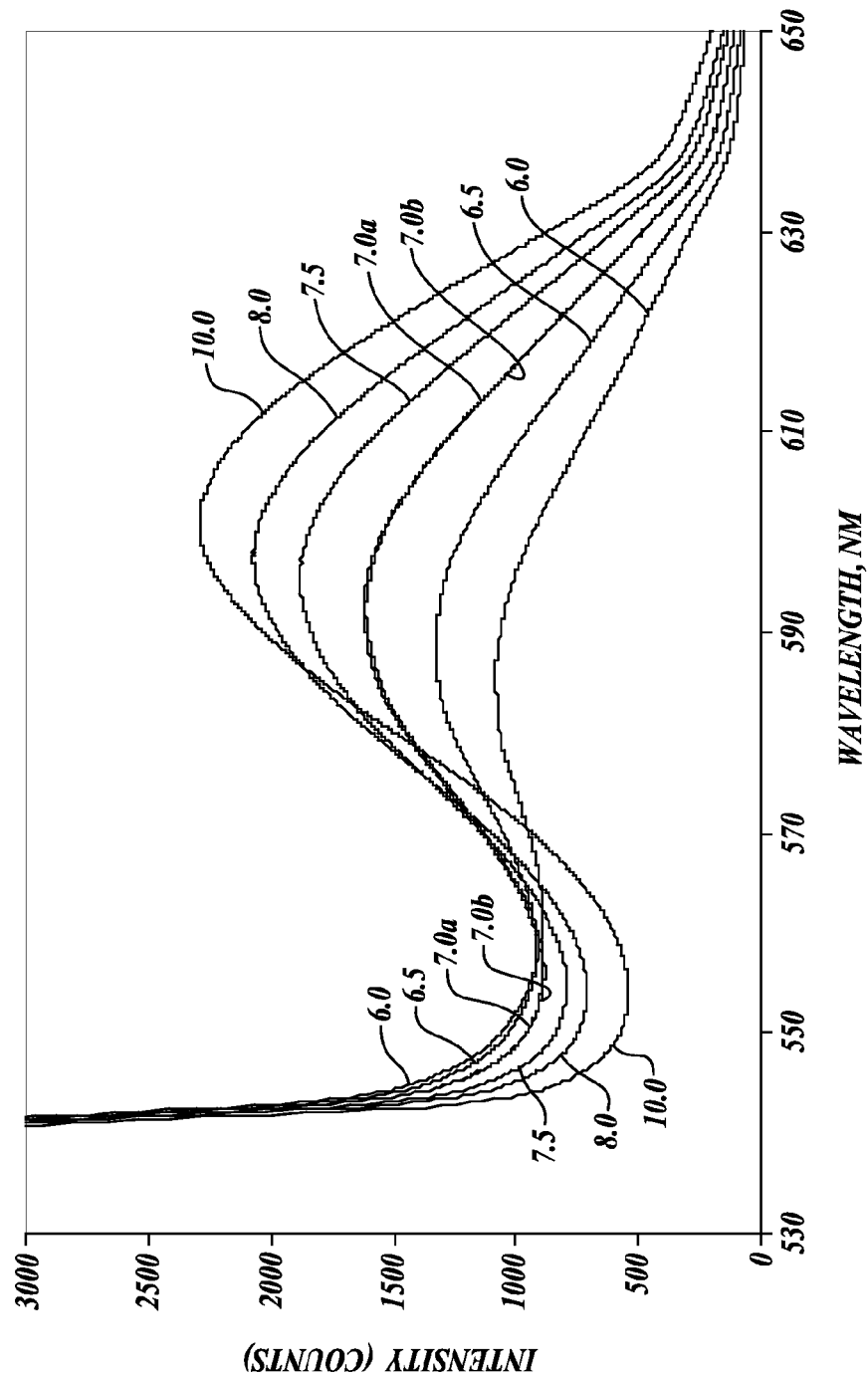
FIG. 15 illustrates the emission spectra of a representative substrate-immobilized fluorophore-protein conjugate (EBIO-3/HSA) as a function of pH (nitrocellulose)

The emission spectra of a representative fluorophore-protein conjugate (EBIO-3/HSA, 2.0:1) immobilized on nitrocellulose, as described in Example 8, as a function of pH (6.0, 6.5, 7.0, 7.5, 8.0, and 10.0), as measured by the telescoping tube insert assay described in Example 11, are illustrated in FIG. 15. The large spread of emissions at 600 nm for the pH 6 to 8 range indicates good fluorescence verses pH response.

Ratiometric pH Method and System. The method of the invention is a fluorescent wavelength-ratiometric method. In the method, the first and second fluorescent emission intensities of the fluorescent species measured at first and second emission wavelengths, respectively, are ratioed to provide pH information. The first emission wavelength varies with pH while the second emission wavelength is constant with pH and gives an internal control for the fluorescent intensity. In one embodiment, a lookup table is used to lookup a combination of the measured ratio, first and second emission wavelength and determines its corresponding pH. In one embodiment, a mathematical function of the ratio, first and second emission wavelength is used to calculate the resulting pH.

Figure 16:
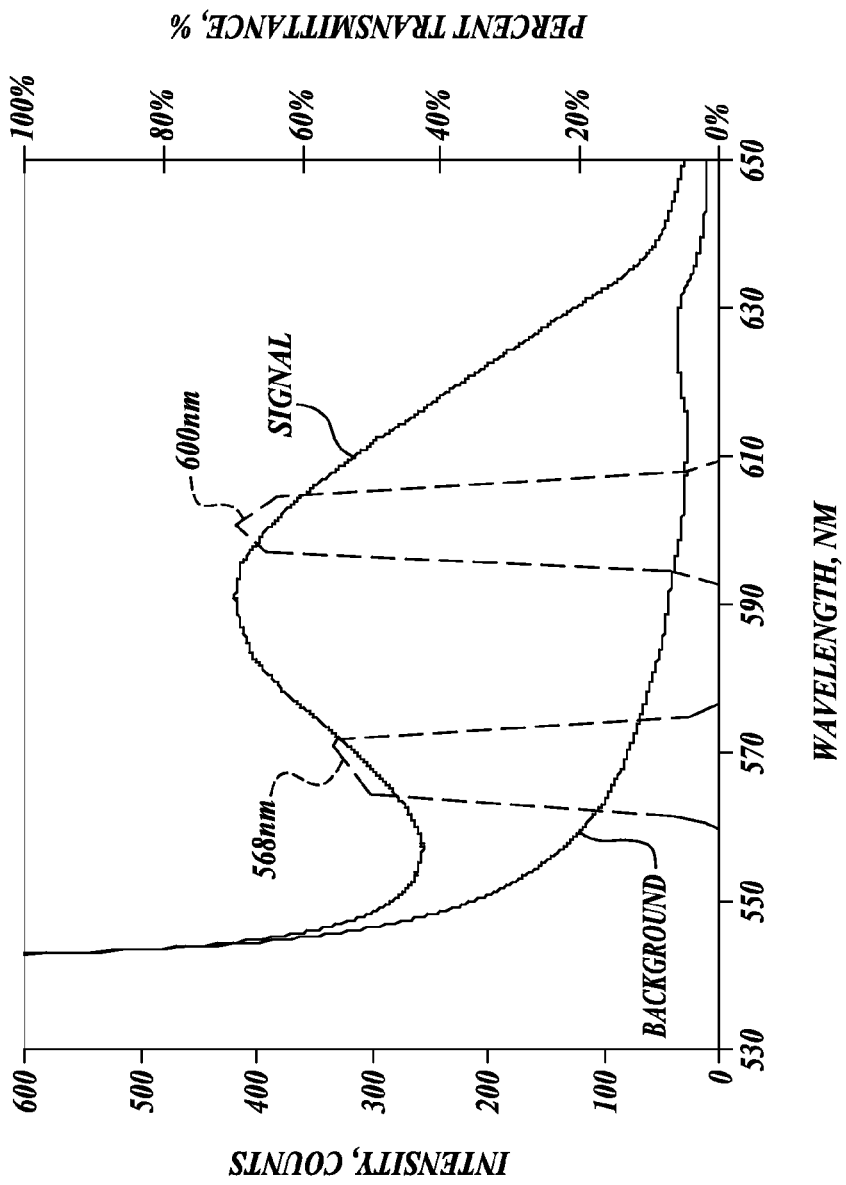
FIG. 16 illustrates the data used in the method of the invention for measuring pH.

FIG. 16 illustrates the data used in the method of the invention for measuring pH. The emission spectra of a representative fluorophore-protein conjugate (EBIO-3/HSA, 2:1) immobilized on nitrocellulose at pH 7.0 is shown as measured by the telescoping tubing insert assay. In this setup, the excitation bandpass filter was unable to completely remove the excitation light in the emission region as illustrated by the background signal measured on a blank nitrocellulose disc. The full spectrum corrected for the background was multiplied by the transmittance of the first and second hypothetical filters at each wavelength and the area under the resultant curve was calculated to give a signal for the first and second wavelength. The center wavelengths and bandwidths of hypothetical filters were chosen such that the ratiometric properties of the conjugate had the strongest relationship to the pH in the region of interest.

Figure 17:
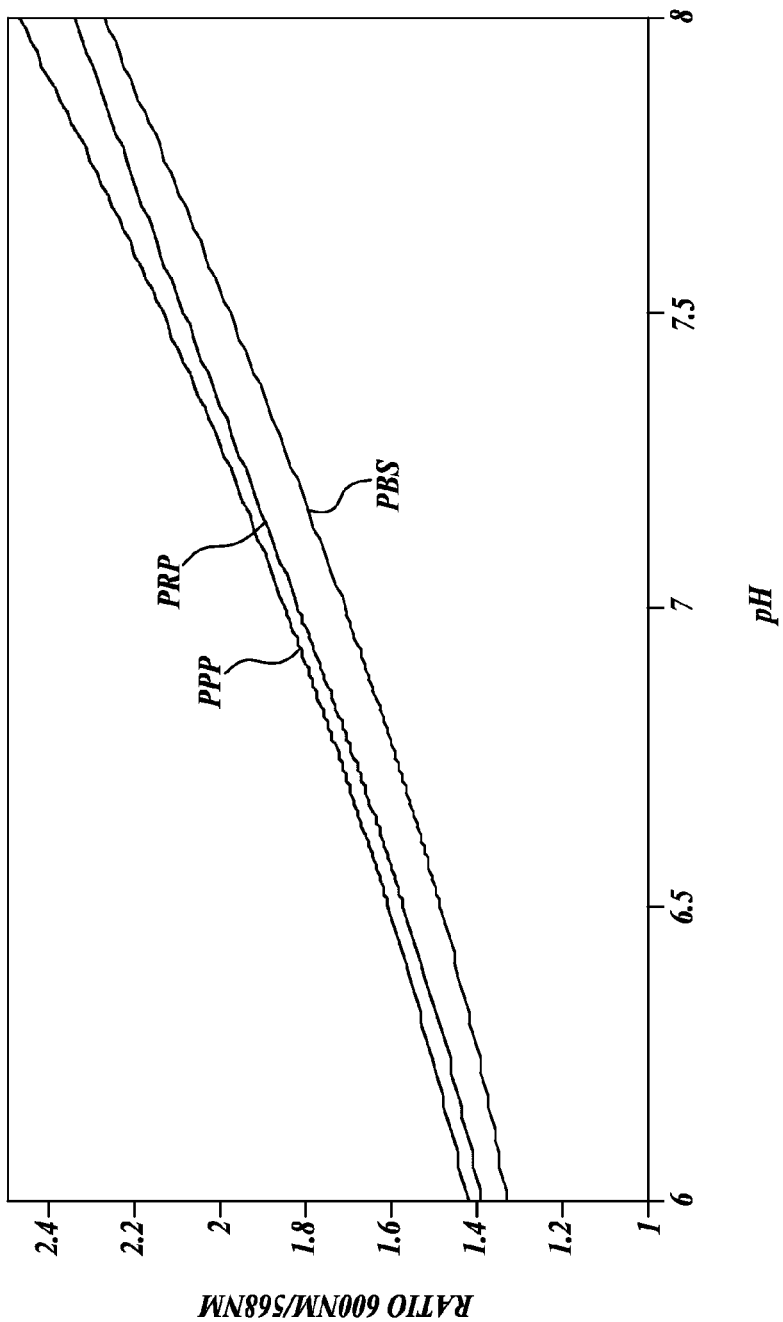
FIG. 17 illustrates the results of the method of the invention for platelet rich plasma.

FIG. 17 illustrates the results of the method of the invention for phosphate buffered saline (PBS), platelet poor plasma (PPP), and platelet rich plasma (PRP) as measured by the telescoping tubing insert assay described in Example 11. The three curves represent the best fit relationship between the measured pH and ratios for the three different liquids.

Figure 18:
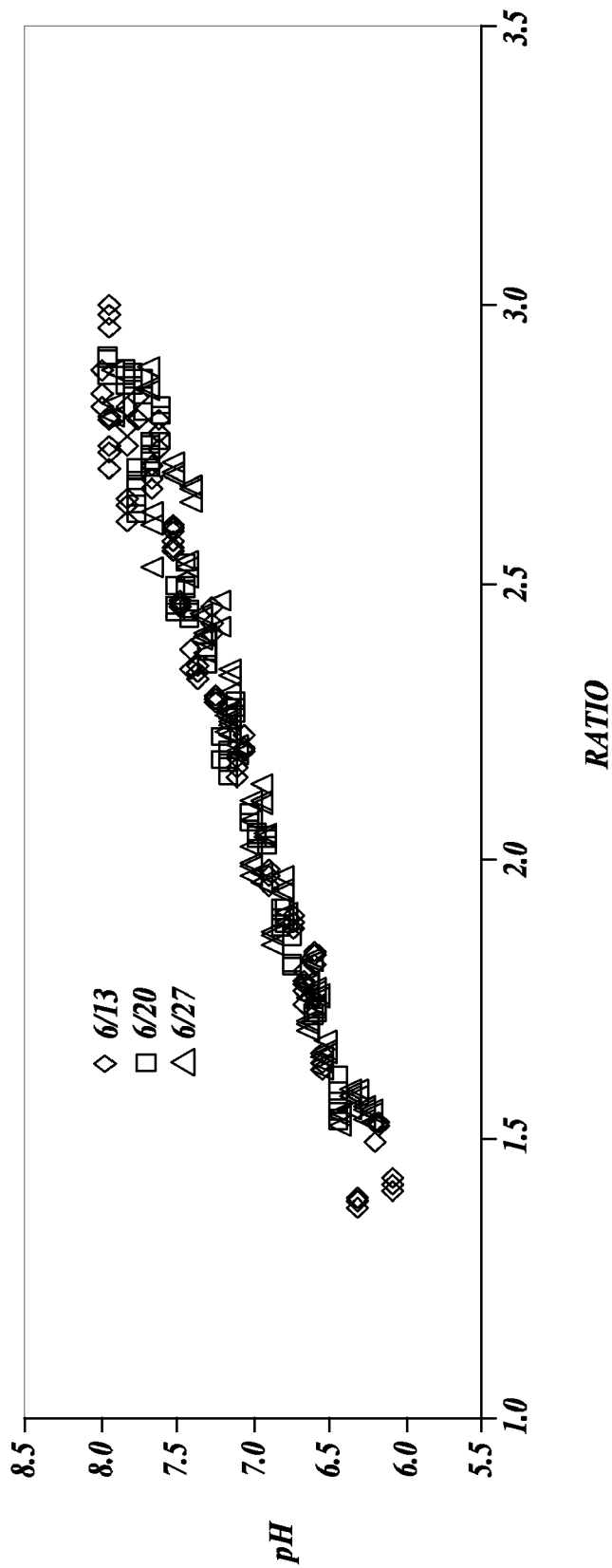
FIG. 18 illustrates the correlation of pH results for platelet rich plasma obtained by the method and system of the invention.

FIG. 18 illustrates the correlation of pH results for three different plasma samples obtained by the method and system of the invention as measured by the injection molded insert PVC tube assay described in Example 11. The relationship between the fluorescent signal and the pH has an accuracy of about 0.1 pH units.

Figure 19:
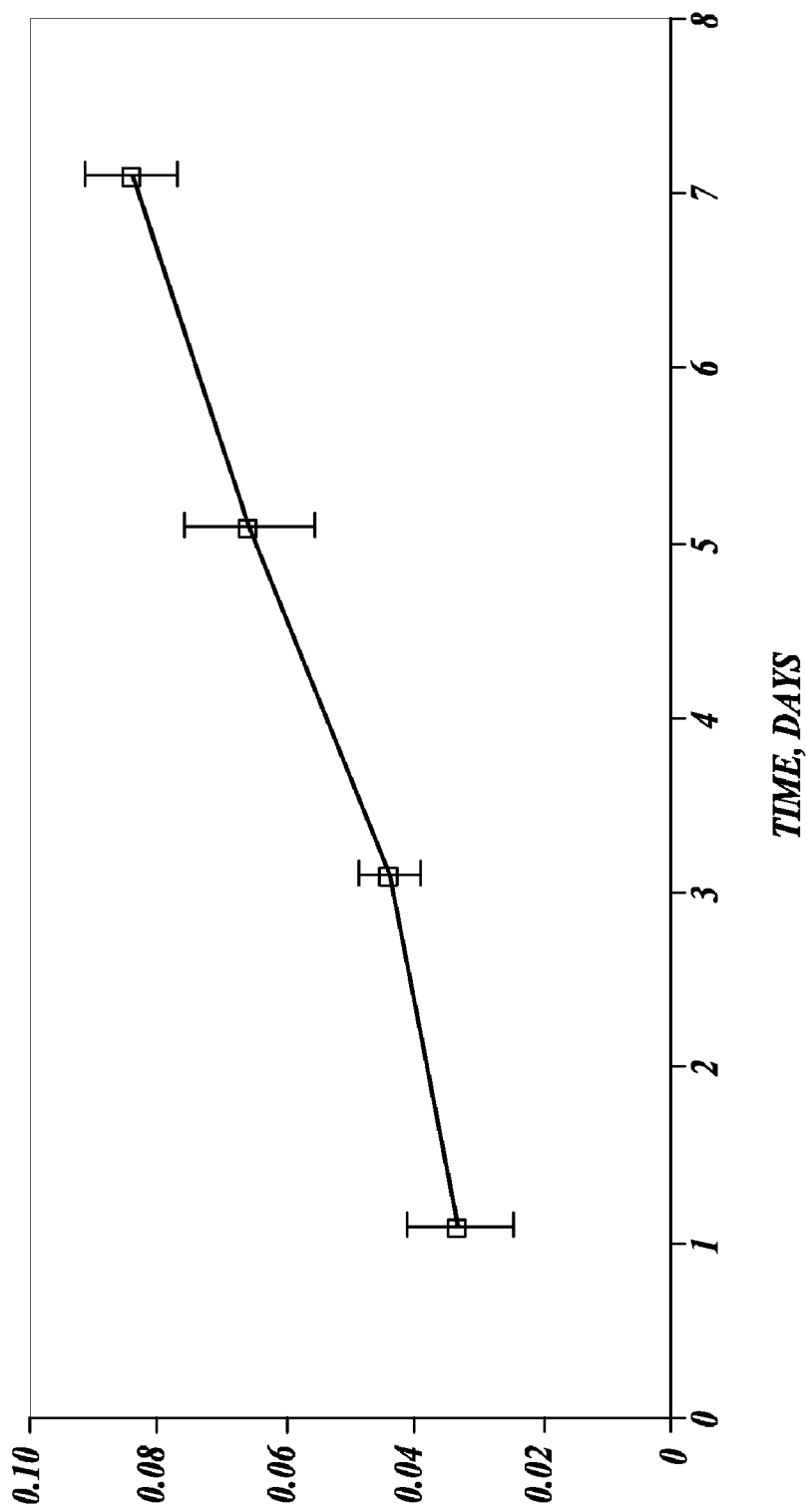
FIG. 19 illustrates stability of a representative substrate-immobilized fluorophore conjugate of the invention.

FIG. 19 illustrates stability of a representative substrate-immobilized fluorophore conjugate of the invention (EBIO-3/HSA, 2:1) on mixed ester nitrocellulose and cellulose acetate prepared by the soaking method and as measured by the leaching assay described in Example 10. The low level of leaching is far below the toxic level for any compound.

Carbon dioxide measurement. In another aspect, the present invention provides a device and method for measuring carbon dioxide concentration in a liquid sample. The carbon dioxide measuring method utilizes the pH measuring method and system described above. In the carbon dioxide measuring method and device, a substrate-immobilized fluorescent species as described above is in contact with a solution, the pH of which is responsive to carbon dioxide level. In addition to being in contact with the substrate-immobilized fluorescent species, the solution having pH responsive to carbon dioxide level is in contact with a liquid sample for which the level of carbon dioxide is to be measured. The solution having pH responsive to carbon dioxide level is isolated from the liquid sample for which the level of carbon dioxide is to be measured by a selectively permeable membrane. The membrane is permeable to gases (e.g., carbon dioxide) and impermeable to other materials (e.g., liquids). Using the method of measuring pH described above, the pH of the solution responsive to carbon dioxide concentration in contact with the substrate-immobilized fluorescent species is measured and correlated with the carbon dioxide level of the sample in contact with that solution.

The solution having pH response to carbon dioxide level is an aqueous solution that includes an agent that is reactive toward carbon dioxide and changes the pH of the solution in response to carbon dioxide concentration. Suitable agents that are reactive toward carbon dioxide and change the pH of the solution in which they are dissolved include bicarbonates, such as sodium bicarbonate.

The selectively permeable membrane isolates the solution having pH responsive to carbon dioxide level from the liquid sample containing carbon dioxide. The membrane is permeable to carbon dioxide and impermeable to liquids and other solutes. In the method, carbon dioxide from the liquid sample passes from the liquid sample through the membrane and into the aqueous solution thereby reacting with the carbon dioxide reactive agent to alter the pH of the aqueous solution. Suitable selectively permeable membranes include membranes made from silicone and PTFE.

Figure 20:
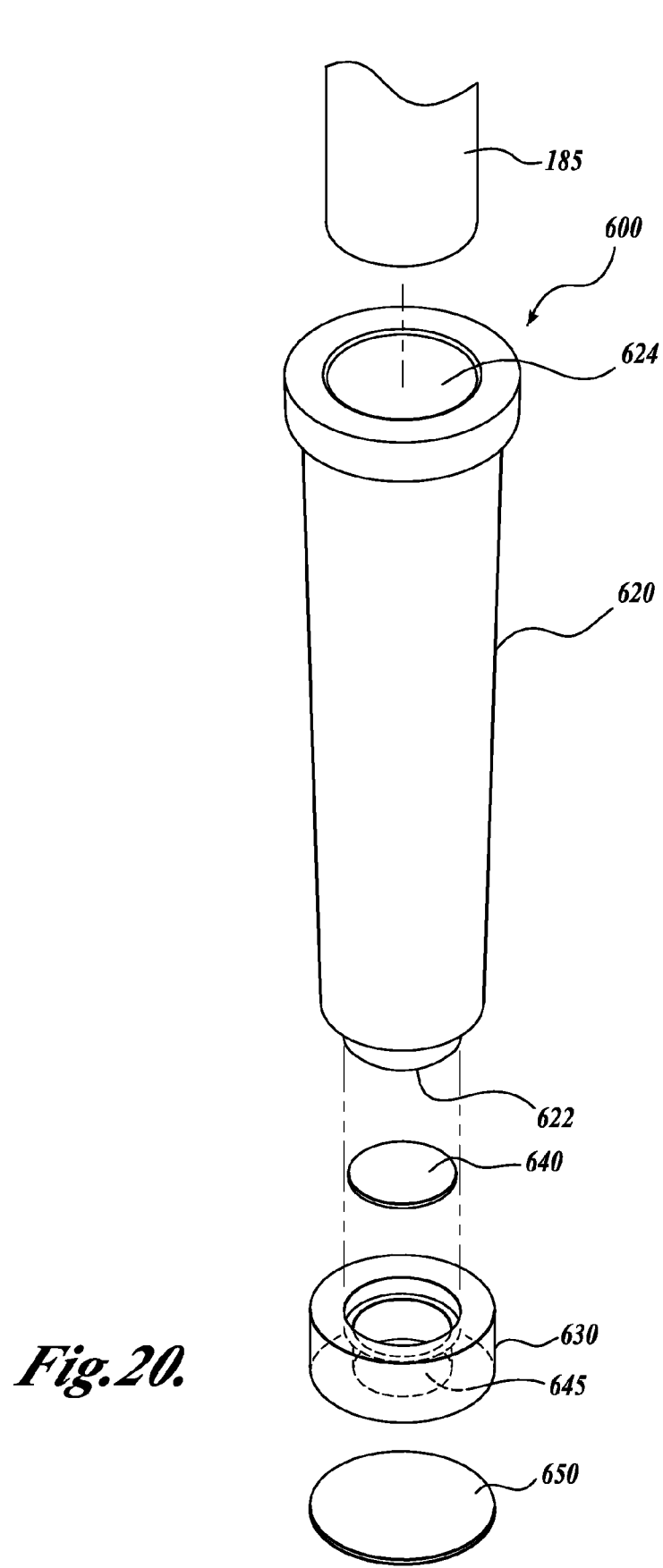
FIG. 20 illustrates a representative device of the invention for measuring carbon dioxide in a sealed vessel.

FIG. 20 illustrates a representative device of the invention for measuring carbon dioxide in a sealed vessel. Referring to FIG. 20, device 600 includes port assembly 610 including port 620 and tip 630. Port 620 is a cylinder terminating with window 622 and having opening 624 for receiving probe member 185. When inserted in the port, the face of probe member 185 and window 622 are substantially parallel. Port 620 and tip 630 are adapted such that the port and tip are reversibly connectable. Substrate 640 including immobilized fluorescent species is secured within port 620 and tip 630. Tip 630 includes a chamber 645 for receiving a solution having pH responsiveness to carbon dioxide. Chamber 645 is defined by window 622, tip 630, and selectively permeable membrane 650. Chamber 645 includes substrate 640, which is interrogated by probe member 185.

A device for measuring carbon dioxide was assembled as described above with the membrane containing immobilized EBIO-3/rHSA conjugate (rHSA is recombinant HSA). A layer of PARAFILM M, a blend of olefin-type materials, was added under the membrane towards the tip. The membrane was hydrated with 5 ul of 35 mM carbonate buffer (pH 7.4), which was sealed within the assembly by the PARAFILM M and remained hydrated throughout the assay. The assembly was subjected to 100% carbon dioxide gas by connection to the gas source with tubing and a "Y" adapter to bleed off the pressure. The assembly was subjected to the carbon dioxide for an allotted period of time, allowed to acclimate to ambient air conditions, and repeated. The fluorescence was measured at each stage at 568 nm and 600 nm after being excited at 525 nm. The results are summarized below in Table 2 and reflect changes in fluorescence due to the change in carbon dioxide concentration demonstrating that the fluorometric ratio method of the invention can also be used to calculate carbon dioxide concentration. The PVC storage bags that are used for platelet storage are somewhat gas permeable, and carbon dioxide is directly related to the measurement of pH.

TABLE 2

Carbon dioxide sensing results.

| Environmental Conditions | EM at 568 nm | EM at 600 nm | Ratio (600/568) |
|---|---|---|---|
| 15 min. at Ambient $CO_2$ | 753 | 2184 | 2.9 |
| 5 min. at 100% CO2 | 1179 | 2234 | 1.894 |
| 15 min. at Ambient CO2 | 833 | 2175 | 2.611 |
| 8 min. at 100% CO2 | 1161 | 1930 | 1.662 |
| 60 min. at Ambient CO2 | 765 | 2184 | 2.854 |

The present invention provides a fluorescence-based pH indicator that can be easily inserted into the sampling ports of designed blood storage bags and interrogated using a fiber optic-based LED light source and photodiode measurement system. This solid state system uses a "ratiometric" calibration method that accounts for variability in fluorescent signal strength due to interfering substances in blood that may interfere with the amount of excitation light that hits the indicator dye. The ratio of fluorescence intensities are measured at two wavelengths, one to detect the acid (protonated) isomer of the dye and one to detect the base (deprotonated) isomer.

To develop an accurate pH detector for platelet rich plasma, compounds having pKa of ~6.6 are suitable, for example, 2-chloro substitution of SNAFL compound lowers the pKa of the phenol from 7.6 to ~6.6. Conjugates of these compounds can be immobilized to various solid supports to provide sensing pH membranes.

The present invention provides an inexpensive, easy to manufacture pH sensing membrane that gives accurate measurement of pH in platelet storage bags at pH 6.5-7.5. In one embodiment, the invention uses a protein conjugate (human serum albumin) of a 2-chloro substituted ratiometric fluorescent compound. The fluorophore:HSA ratio was optimized for performance when immobilized to a nitrocellulose blot membrane. After drying on the membrane, the fluorophore:HSA conjugate has very low leaching rates. Discs of this material are easily assembled into holders for insertion into the sampling ports of platelet storage bags. The fluorescent membrane materials showed good pH response using a green LED based fluorometer. In the method, two emission wavelengths for ratiometric pH detection are measured with properly filtered photodiodes with an accuracy of ~0.1 units at the desired low pH threshold of 6.5.

Fluorescent probe molecules can be designed to be sensitive to a variety of environments. The method and system of the invention describes the use of pH-sensitive fluorophores. However, other environments can be interrogated by the method and system of the invention modified to include environment-sensitive fluorophores other than pH-sensitive fluorophores. A variety of fluorescent probes that change fluorescent properties as the molecular environment changes are commercially available. See, for example, Molecular Probes Handbook (9th Edition) by R. P. Haugland. Probes can be linked to albumins or other proteins and used to prepare substrates for interrogation as described in herein or using other fluorescent-based methods. Examples of environment-sensitive fluorophores, systems, and methods include the following.

Nucleic acid detection: nucleic acid binding dyes change fluorescent properties in the presence of DNA or RNA.

Enzyme substrates: proteins or peptides can be labeled with fluorescent dyes and fluorescent quenching molecules such that a fluorescent signal is generated in the presence of particular enzymes such as proteases (FRET detection).

Probes for lipids: lipophilic dyes can change fluorescent properties in the presence of cell membranes or other lipid rich analytes.

Probes for oxygen: in addition to pH detection and carbon dioxide detection, certain fluorescent molecules are sensitive to changes in oxygen concentration, for example, tris(2,2'-bipyridiyl)ruthenium(II) dichloride (RTDP).

Indicators for metal ions: fluorescent dyes that bind metals can change fluorescent properties upon binding calcium, magnesium, zinc, sodium, potassium, among other.

Glucose detection: certain lectins such as ConA bind glucose, and suitably labeled lectins can be prepared as probes for glucose.

The following examples are provided for the purposes of illustrating, not limiting, the invention.

EXAMPLES

Example 1

The Manufacture of a Vessel Incorporating a Representative Substrate-Immobilized Fluorescent Species Referring to FIG. 5B, sealed vessel 500 is manufactured from PVC. PVC material is compounded with a number of additives, for example, plasticizers, stabilizers, and lubricants. The formulation is used for making bags and tubes. The compounded PVC is extruded through a die for converting the plasticized material into sheet form. The extruded sheet, after slitting, is cut into the desired size and sent to the welding section. The donor and transfer tubings are made by extrusion of similar PVC compounds. The tubes are then cut to the appropriate length and sent to the welding section. The components, such as transfusion ports, needle covers, and clamp, are produced by injection molding. The components are ultrasonically cleaned and dried in a drying oven.

Welding. The blood bags are fabricated by a high frequency welding technique. Sized PVC sheets are placed between electrodes and high frequency at high voltage is applied. PVC gets heated very rapidly and sealing takes place between electrodes. Transfusion ports and donor and transfer tubing are kept in the appropriate position with the bag and welded to form an integral part of the blood bag system. For the manufacture of a vessel incorporating a representative substrate-immobilized fluorescent species (FIG. 5B), an open tube is welded to provide port 510A. The tube can be made of colored PVC to provide light protection for the immobilized fluorescent species. Welded bags are trimmed. The port assembly 232 (FIG. 6) is manufactured from injection molded Lexan parts (205 and 235) and a 3.53 mm (9/64 inch) diameter nitrocellulose disc with immobilized fluorescent species (220). The port assembly is held together by friction fit or can be glued in place. The port assembly is inserted in the open tube of port 510A. The port assembly is held in the port by friction fit or can be glued in place. The assembled bag and port assembly is sterilized and labeled for ultimate storage of platelet concentrates.

Example 2

The Incorporation of a Representative Substrate-Immobilized Fluorescent Species into a Sealed Vessel Referring to FIG. 5A, sealed vessel 500 includes a plurality of vessel ports 510. Port assembly 202 resides in vessel port 510A after insertion. The port assembly 202 (FIGS. 4A-4C) is manufactured from injection molded Lexan parts (205 and 215) and a 3.53 mm (9/64 inch) diameter nitrocellulose disc with immobilized fluorescent species (220). The port assembly is held together by friction fit or can be glued in place. The port assembly is inserted through the septum seal inside port 510A by puncturing the seal with the spiked tip. Alternatively, the seal can be pre-punctured with a separate spike tool. The insertion of the port assembly can be performed on either empty or platelet filled bags, but in either case, aseptic methods should be used to avoid possible contamination of the bag contents. The port assembly is held in the port by friction fit or can be glued in place. Vessel 500 remains sealed (leakproof) after insertion of port assembly 202 in port 510A.

Example 3

Fluorescence and pH Properties of Representative SNAFL Analogs: pKa Determination Instrumentation. Fluorescence versus pH of various SNAFL free acids were compared using an Ocean Optics USB2000 fiber optic spectrometer and a tungsten halogen light source (part number HL-2000 FHSA). The light source was equipped with a linear variable filter that allowed the wavelength and shape of the excitation beam to be adjusted. The excitation wavelength was adjusted by using a blank cuvette to the absorbance max of the fluorophore (see Table 1). A cuvette holder (part number CUV-FL-DA) was directly attached to the light source and a fiber optic cable directed emitted light to the spectrometer. Excitation conditions are reported for each fluorescence spectrum (3000 msec irradiation at the indicated wavelength). Spectral data were collected on a personal computer using the Ocean Optics software and overlays of different spectra were captured.

Sample preparation. SNAFL-1 was purchased as the free carboxylic acid from Molecular Probes in a 1 mg vial. 0.3 mL of isopropyl alcohol and 0.7 mL of water was added to make a 1 mg/mL solution. A molecular weight (MW) of 426 for SNAFL-1 was used to calculate molarity (SNAFL-1=2.35 mM). 4.25 uL of this solution was diluted to 1 mL with various 50 mM phosphate buffers to give 10 micromolar solutions with pH 6-10. 10 micromolar solutions of SNAFL-2 (MW=460) were prepared in a similar fashion. EBIO-1 (MW=523), EBIO-2 (MW=627), and EBIO-3 (MW=489) were obtained as bulk compounds from Epoch Biosciences. 1.6 mg of each solid powder was carefully weighed out and dissolved in 3.2 mL of 40% isopropyl alcohol to give 0.5 mg/mL solutions. Emission spectra were obtained for the various SNAFL and EBIO compounds at pH 6.0, 6.2, 6.4, 6.6, 6.8, 7.0, 8.0 and 10.0. Examples of overlayed fluorescence emission spectra are shown in FIG. 8 (SNAFL-1) and FIG. 9 (EBIO-3). All spectra showed an isosbestic wavelength where all emission spectra overlap (See Table 1). This is a characteristic of ideal ratiometric performance with no competing fluorescent structures other than those shown above (lactone, naphthol, naphtholate).

pKa calculations. The pH at which two molecular species (tautomers) are equally represented is defined as the pKa. There are many variables that can affect pKa and methods for measurement are difficult since the structures have overlapping absorbance. Therefore direct comparisons from the literature can vary slightly. The calculations contained herein are based on the assumption that, at pH 10, only the trianionic naphtholate structure is present. The intensity of fluorescence at the emission maxima is divided by 2, and pH of the intersecting pH curve is calculated by interpolation between the nearest 2 curves. The pKa of the 2-chloro substituted EBIO compounds is significantly lower than the other analogs as shown in Table 1.

Example 4

The Preparation of Representative Fluorophore-Protein Conjugates: SNAFL-1/HSA

Human serum albumin (HSA) was purchased from Sigma (catalog #A-8763) as 100 mg of lyophilized powder. SNAFL-1 NHS ester was purchased from Molecular Probes as a mixture of the 5 and 6 isomers. A solution of 10 mg (0.15 micromoles) of HSA in 1 mL of pH 8.56 sodium bicarbonate (0.1 M) was prepared. A solution of 1 mL (1.91 micromoles) of the NHS ester in 0.1 mL of dimethylsulfoxide was prepared. 0.3 mL aliquots of the HSA solution were transferred to a 1.6 mL Eppendorf tubes and various offering ratios of the NHS ester solution were added: tube 1, 11.8 microliters (5 equivalents); tube 2, 23.6 microliters (10 equivalents), tube 3, 47.1 microliters (20 equivalents). The deep red solutions were vortexed and allowed to stand in the dark for at least one hour. The 5:1 conjugate from tube 1 was purified by gel filtration chromatography on a 0.5×20 cm column packed with Sephadex G-15 and pH 7.4 phosphate buffered saline (PBS). The conjugate was isolated as a fast moving red/orange band in PBS and diluted to 0.75 mL with PBS to give a 4 mg/mL solution of the protein conjugate. Most of the color eluted with the conjugate, but some small molecular weight (orange) impurities remained on top of the column. The column was clean enough to be re-used for purification of the 10:1 and 20:1 conjugates. Each was eluted in PBS and diluted to 0.75 mL to give ~4 mg/mL solutions (60 micromolar based on HSA component). The red solutions were stored refrigerated and protected from light. 1 micromolar solutions of each SNAFL-1/HSA conjugate were prepared and analyzed by UV-vis spectra using a Beckman DU640B spectrometer. Each spectrum showed absorbance maxima at 490 and 521 nm at pH 7 as expected for the acid form of SNAFL-1 conjugates. The relative absorbance showed the expected change in absorbance with different SNAFL:HSA offering ratio. A 10 micromolar solution of SNAFL-1 acid (obtained from Molecular Probes) at pH 7 was used as a standard to more accurately determine the average loading of SNAFL-1 per each HSA conjugate preparation. Using this assay, the 5:1 conjugate had 4.1 fluors/HSA, the 10:1 conjugate had 6.4 fluors/HSA, and the 20:1 conjugate had 11.2 fluors/HSA.

Example 5

The Fluorescent Properties of Representative Fluorophore-Protein Conjugates: SNAFL-1/HSA Relative fluorescence of various SNAFL-1/HSA conjugates and SNAFL-1 free acid were compared using an Ocean Optics USB2000 fiber optic spectrometer and a tungsten halogen light source (part number HL-2000 FHSA). The light source was equipped with a linear variable filter that allowed the wavelength and shape of the excitation beam to be adjusted. A cuvette holder (part number CUV-FL-DA) was directly attached to the light source and a fiber optic cable directed emitted light to the spectrometer. Excitation conditions are reported for each fluorescence spectrum (3000 msec irradiation at the indicated wavelength). Spectral data were collected on a personal computer using the Ocean Optics software and overlays of different spectra were captured. A comparison of various loading levels of SNAFL-1/HSA showed that 4.1 to 1.6 SNAFL-1 molecules gave about the same fluorescent signal. Higher loading or lower loading conjugates gave lower signals.

Emission spectra were obtained for 10 micromolar solutions in potassium phosphate buffer. Excitation was at 540 nm. Emission maximum at 620 nm was observed for the base form of SNAFL-1 (pH 10). As expected, intensity of 620 nm fluorescence decreased as pH decreased. An isosbestic point at 585 nm, where fluorescence remained constant at all pH, was observed. Response was good at about pH 8, but poor between pH 6-7.

Spectra obtained for a 2.5 micromolar solution of a representative SNAFL-1/HSA conjugate (1.6 SNAFL-1/HSA) showed improved pH response for pH 6-7 (see FIG. 11). The Ocean Optics halogen light source was equipped with a 532 nm interference filter (Edmund Optics, Barrington, N.J.) and this allowed the fluorescent isosbestic point at 572 nm for pH 6-7 to be detected. Emission maximum at 620 nm was observed for the base form of SNAFL-1 (see pH 10 curve). As expected, intensity of 620 nm fluorescence decreased as pH decreased. In comparison to the free SNAFL-1 carboxylic acid (see FIG. 8) improved response for pH 6-7 was observed for the HSA conjugate. A red shift of the pH 8 and 10 curves from the isosbestic wavelength was observed, indicative of other competing molecular structures involving the fluorescent species. This non-ideal behavior may be eliminated by use of a longer linker structure or a more hydrophilic linker structure between the fluorescent dye and the HSA spacer.

Example 6

The Preparation of Representative Fluorophore-Protein Conjugates: EBIO-3/HSA

Method A. A 0.1 M stock solution of EDC (Sigma/Aldrich Chemical Co., St. Louis Mo.) was prepared by dissolving 6.2 mg of EDC in 0.2 mL of DMF and 0.123 mL of 50 mM phosphate buffer (pH 5.8). 1.0 mg of EBIO-3 acid (Nanogen, Bothell, Wash.) was dissolved in 0.102 mL of DMF to give a 20 mM solution. 3.0 mg (0.045 micromoles) of HSA (Sigma/Aldrich Chemical Co., St. Louis, Mo.) was dissolved in 0.3 mL of pH 8.5 sodium bicarbonate in each of two 1.7 mL Eppendorf tubes. 0.1M EDC (0.045 mL) was added to 20 mM EBIO-3 (0.045 mL, 0.9 micromoles) in a separate Eppendorf tube and this was added to one of the HSA tubes to give an EBIO-3:HSA offering ratio of 20:1. An offering ratio of 5:1 was used in the other HSA tube by adding a premixed solution of 0.0225 mL of EDC (0.1 mM) and 0.0225 mL of EBIO-3 (20 mM). The homogeneous dark red HSA conjugate solutions were incubated at room temperature in the dark. After 21 hours, each of the HSA conjugates was purified on a G15 Sephadex column as described above for the SNAFL conjugates (Example 4). Some unreacted EBIO-3 acid remained at the top of the column (especially for the 20:1 offering ratio), but was cleanly separated from the desired protein conjugate that eluted first as a pink fraction in ~0.5 mL of pH 7.4 buffer. Each of the purified conjugates was diluted to 0.75 mL with pH 7.4 PBS to give 4 mg/mL solutions (0.06 mM). The red solutions were stored refrigerated and protected from light. 1 micromolar solutions of each EBIO-3/HSA conjugate were prepared at pH 7.4 and analyzed by UV-vis spectra using a Beckman DU640B spectrometer. The free EBIO-3 acid (10 micromolar) spectrum had absorbance maximum at 534 nm, the 20:1 conjugate had absorbance at 538 nm and the 5:1 conjugate had maximum at 545 nm. The spectra showed the expected increase in absorbance with increasing EBIO-3:HSA offering ratio. Using this EBIO-3 acid as a standard, the 20:1 conjugate had 5.07 EBIO-3:HSA and the 5:1 offering had 1.92 EBIO-3:HSA. The coupling efficiency was somewhat lower than for the SNAFL/HSA conjugates of Example 4 (the 20:1 conjugate had 11.2 fluors/HSA and the 5:1 offering had 4.1 fluors/HAS). The EDC coupling method was suitably efficient and reproducible.

Method B. A 0.1 M solution of EDC (Sigma/Aldrich Chemical Co., St. Louis, Mo.) is prepared by dissolving 6.0 mg of EDC in 0.194 mL of DMF and 0.118 mL of 50 mM PBS (pH 7.4). 3.0 mg of EBIO-3 acid (Nanogen, Bothell, Wash.) is dissolved in 0.306 mL of DMF to give a 20 mM solution. The two solutions are combined in the EBIO-3 solution container and incubated at room temperature for one hour in the dark. 75.0 mg (1 micromole) of liquid recombinant HSA (rHSA) from yeast (Delta Biotechnology, Ltd., Nottingham, UK) is mixed with 7.5 mL of pH 8.5 sodium bicarbonate in a 15 mL conical tube. The entire contents of the EBIO-3/EDC solution are combined with the rHSA solution and incubated at room temperature in the dark for 15-20 hours. The rHSA/EBIO-3 conjugate is purified using the Amicon stirred ultrafiltration cell system and a YM10 membrane (Millipore, Bedford, Mass.). A 50 mM PBS (pH 7.4) is used as the wash solution. After purification, the protein concentration of the conjugate is measured using the BCA™ Protein Assay (Pierce, Rockford, Ill.). An aliquot of the conjugate is diluted to 1 mg/ml with 50 mM PBS (pH 7.4) based on its BCA determined protein concentration. The 1 mg/ml aliquot of conjugate, the last milliliter of PBS effluent, an aliquot of the 50 mM PBS (pH 7.4), and an aliquot of the EB3 Standard (15 mM EBIO-3 solution in DMF and 50 mM PBS (pH 7.4)) are analyzed via an absorbance scan utilizing Bio-Tek's Synergy HT plate reader. The scan is taken on 300 microliters of each of the above mentioned samples in a black, 96-well, clear, flat bottom plate, scanned from 450 nm to 650 nm. Their max peaks are recorded and used to determine purity and quality of the conjugate.

Example 7

The Fluorescent Properties of Representative Fluorophore-Protein Conjugates: EBIO-3/HSA Fluorescence spectra were obtained for 2.5 micromolar solutions of the two EBIO-3/HSA conjugates prepared as described in Example 6 (Method A). The conjugates showed improved pH response for pH 6-7 (see FIG. 12 for overlayed spectra for the 1.92:1 EBIO-3/HSA conjugate). The Ocean Optics halogen light source was equipped with a 532 nm bandpass filter (Edmund Optics, Barrington N.J.) and this allowed the fluorescent isosbestic point at ~565 nm for pH 6-7 to be detected. Emission maximum at 605 nm was observed for the base form of SNAFL-1 (red trace, pH 10). As expected, intensity of 605 nm fluorescence decreased as pH decreased. In comparison to the SNAFL-1/HSA conjugate (see FIG. 11) improved response for pH 6-7 was observed for the EBIO-3/HSA conjugate. A red shift of the pH 8 and 10 curves from the isosbestic wavelength was observed, indicative of other competing molecular structures involving the fluorescent species, but was of smaller magnitude than for the SNAFL-1/HSA conjugate.

Example 8

Immobilization of Representative Fluorophore-Protein Conjugates: SNAFL-1/HSA

Fluorophore-protein conjugates and fluorophore-carbohydrate conjugates were immobilized on either nitrocellulose or capillary pore membranes using the following general method. Fluorescein labeled dextrans with "fixable" lysine residues were obtained from Molecular Probes. These dextrans had a molecular weight of about 10,000 1.8 fluorophores per conjugate, and 2.2 lysines per conjugate and are sold under the trade name "Fluoro-Emerald". Fluorescein labeled bovine serum albumin (BSA) was also obtained from Molecular Probes and had 4.5 fluors per conjugate. Various SNAFL-1/HSA conjugates were prepared as described in Example 4. Nitrocellulose membranes were obtained from Schleicher and Schuell under the trade name PROTRAN. Pore diameter was reported as 0.2 microns. Capillary pore membranes made from polyester films were obtained from Oxyphen in a variety of pore sizes. 0.1 micron and 1.0 micron pore size membranes were successfully used to immobilize fluorescein dextrans. Fluorescein/dextran, fluorescein/BSA and SNAFL-1/HSA conjugates were all successfully immobilized and the fluorescent properties of the SNAFL-1/HSA conjugates were fully characterized as described as follows.

General Immobilization Method. SNAFL-1/HSA (2.5 SNAFL-1/HSA) on 0.1 micron pore diameter Oxyphen Membrane Discs. Fluorescent HSA conjugates with a 2.5:1 SNAFL-1:HSA offering ratio were prepared as described in Example 4 and diluted to provide concentrations of 0.05, 0.2, 1.0 and 4 mg/mL in phosphate buffered saline (PBS) (pH 7.4). 5 microliter drops were applied via a 20 microliter pipettor to the center of pre-punched porous discs (¼ inch diameter) that were laid on a bench top. The spotted discs were allowed to air dry (about 30 minutes) and then placed in separate desiccators overnight. The dried discs were washed in separate Eppendorf tubes with 2×1 mL of PBS and allowed to soak overnight in 1 mL of PBS. The washed discs were stable in PBS solution (no degradation after 30 days). Alternatively the discs could be re-dried in desiccators and stored dry. The wet or dry stored discs had comparable fluorescent properties. The discs had fluorescent signals that were proportional to the concentration of labeled macromolecule applied to each one as measured by the fluorescence assay described in Example 9.

Example 9

The Fluorescent Properties of Representative Immobilized Fluorophore-Protein Conjugates: SNAFL-1/HSA Microwell assay of fluorescent macromolecular conjugates on porous membrane discs using a fiber optic spectrometer. Fluorescent discs prepared as described in Example 8 were examined for fluorescent properties using the Ocean Optics fiber optic spectrometer described in Example 5. The cuvette on the light source was replaced by a fiber optic reflectance probe which had 6 excitation fibers wrapped around a single fiber that picks up the emitted light from the sample and sends it to the spectrometer. The reflectance probe was threaded through a hole in a 12×12×18 inch black box with a lid on the front. The probe was clamped inside under a 1 cm square opening that allowed the tip of the probe to be positioned under a 96-well micro well plate (clear bottom black plate). The probe was tilted at a 30 degree angle to reduce reflected light entering the probe tip. The fluorescent disc of interest was placed in the bottom of a well and covered with 300 microliters of the analyte solution of interest. The excitation light source was turned on long enough to position the disc of interest over the tip of the reflectance probe, then the shutter was closed and the plate was covered with another box to shield the disc from ambient light. Unless otherwise mentioned, the Ocean Optics software was set to collect data with a 3000 msec integration time and 3 averages. A dark spectrum was captured with the shutter closed and used for all background subtracted readings during the assay. The shutter was then opened and fluorescent reading of the disc was started. The graphical display on the computer screen gave real-time spectra after each 3000 msec integration time. After the required 3 spectra were obtained (about 10 seconds) the graphical display showed only subtle changes. At this point a snapshot of the displayed spectrum was captured and saved to disc for future processing. The shutter was closed, and the next microwell experiment was set up. The same disc could be measured multiple times by exchanging the analyte solution in the microwells. Alternatively, different discs in different wells could be measured by re-positioning the microwell plate over the reflectance probe.

Fluorescent loading of SNAFL-1/HSA immobilized on Oxyphen discs. The microwell assay described above was used to compare the relative-fluorescence of SNAFL-1/HSA on Oxyphen discs. The excitation filters in the halogen light source were set to a wavelength of 532 nm and a "wide open" bandpass position to maximize sensitivity of the assay. Reflectance of the excitation beam back into the detector fiber was significant, and the wavelength position of the filter was adjusted to provide a "minimum" at 620 nm where the fluorescence from the base form of SNAFL-1/HSA is greatest. The various concentrations of SNAFL-1/HSA described in Example 8 were examined in separate microwells in pH 7 potassium phosphate buffer (50 mM) as described above. The spectra showed the ability to distinguish relative fluorescence intensity of 4, 1, 0.2 and 0.05 mg/mL membranes at pH 7. All had signal greater than background.

Relative fluorescence intensity of various amounts of SNAFL-1/HSA (2.5:1) immobilized on porous Oxyphen discs at pH 7. The fluorescent intensity was measured at 620 nm, the fluorescent maximum of the base form of the fluorophore. Excitation used a wide open setting on the halogen lamp that efficiently excites both acid and base forms of SNAFL-1. The reflected light from the source (unmodified disc) had the lowest intensity spectrum. The spectrum of the 0.05 mg/mL disc gave a small increase in fluorescence intensity. The 0.2 mg/mL disc, 1 mg/mL disc, and 4 mg/mL disc showed stepwise increases in fluorescence intensity. The fluorescence spectra of two 30 day PBS soaked sample (1 mg/mL) from a different batch of membranes were essentially the same and showed that membrane loading was reproducible from batch to batch, and that the SNAFL-1/HSA conjugates did not dissociate significantly from the disc surface in PBS solution.

pH Dependent fluorescence of SNAFL-1/HSA immobilized on Oxyphen discs. The 1 mg/mL SNAFL-1/HSA discs described above were examined for pH dependent response in the microwell assay. A single disc was examined in potassium phosphate buffers of pH 4, 5, 6, 7, 8, 9, and 10. The data showed that these membrane discs had a wide dynamic range of pH measurement, but had more sensitive response at pH>6. The time between buffer exchanges was 5 min, and there was no significant change in spectra after additional equilibration time. This showed that the response time for even dramatic changes in the pH environment of the immobilized SNAFL-1/HSA conjugates is rapid.

"Crossover assay" for fluorescence measurement of pH using SNAFL-1/HSA Oxyphen discs. The microwell assay described above was used to examine the fluorescent isosbestic properties of the discs. For this assay, the shutter assembly in Ocean Optics halogen light source (part number HL-2000 FHSA) was removed, and two 532 nm bandpass filters (Edmund Scientific) were inserted in the cavity using a special adaptor. This dramatically reduced the reflected background in the spectral region of interest (>550 nm). The data shown are for 4 mg/mL loading discs prepared with SNAFL: HSA (5:1) conjugate. The immobilized protein conjugate showed unusual pH vs. fluorescence properties in comparison to the solution phase data. Instead of a fluorescent isosbestic point at 575 nm, there was a stepwise increase in the fluorescent intensity as pH increased. The pH 10 spectrum showed the expected maximum at 620 nm, and crossed the overlaid spectral curves obtained in pH 4, 6, 7 and 8 buffers. These "crossover points" were used as the basis for a sensitive assay to determine pH of the membrane environment. Three different membrane discs were examined using this assay format on three different days. The crossover points were reproducible within 2 nm.

The 4 mg/mL discs (3.6:1 SNAFL-1:HSA) showed stepwise increase in pH 10 "crossover". The crossover was at 579 nm for pH 4. Three discs/three different days gave the same result±2 nm. The crossover points were at 592 nm (pH 6), 600 nm (pH 7a,b), and 611 nm (pH 8). The fluorescent maximum at pH 10 was at 620 nm, similar to the solution phase properties.

Example 10

Immobilization of Representative Fluorophore-Protein Conjugates: EBIO-3/HSA Spotting Immobilization Method. EBIO-3/HSA conjugate was prepared as described in Example 6 at a ratio of 2:1. Nitrocellulose membranes were obtained from Schleicher and Schuell under the trade name PROTRAN. The discs were treated in the same way as the general immobilization method described in Example 5 using a 4 mg/ml solution of EBIO-3/HSA.

Soaking Immobilization Method. EBIO-3/HSA conjugate was prepared as described in Example 6 at a ratio of 2:1. Mixed ester nitrocellulose and cellulose acetate membranes were obtained from Millipore under the product series TF. The EBIO-3/HSA conjugate is diluted to 0.2 mg/ml and 45 ml is added to a 9 cm disc of the membrane. The disc is agitated overnight at room temperature and protected from light. The unbound conjugate is removed and the disc is washed with two 1 hour washes and one overnight wash all with agitation.

The disc is then desiccated and stored dry. Smaller discs are punched from the 9 cm disc for studies.

Example 11

The Fluorescent Properties of Representative Immobilized Fluorophore-Protein Conjugates: EBIO-3/HSA Telescoping tubing insert assay of fluorescent macromolecular conjugates on porous membrane discs using a fiber optic spectrometer. Fluorescent discs prepared as described in Example 10 were examined to relate the fluorescent properties to the liquid phase pH using the Ocean Optics fiber optic spectrometer described in Example 9 with the dual 532 nm filtered (Edmund Scientific) halogen light source (part number HL-2000 FHSA). A holder for a 5/32 inch membrane disc was crafted with 4 mm OD and 5 mm OD polystyrene telescoping tubing and an angled 0.015 in thick polystyrene window. The angled window was placed so that it held the membrane disc at a 60 degree angle relative to the tubing axis. This allows the fiber optic probe to be placed in one end of the tubing and interrogate the disc on the other side of the window which is contact with a liquid of a certain pH. Buffers of known pH values were placed in contact with the telescoping tubing inserts and discs made by the spotting immobilization method in Example 10 and fluorescent emissions recorded with the Ocean Optics software set to collect data with a 1000 msec integration time and 3 averages.

For liquids with unknown pH values, a stirred and light protected vessel containing 5 telescoping tubing inserts and discs made by the soaking immobilization method in Example 10, 50 mL of buffer or plasma, and a calibrated pH electrode (ROSS electrode/Orion 720a meter) was used to study the pH and fluorescent response of the fluorescent discs. Drops of 1 N HCl or 1 M NaOH were added to create a range of pHs from liquids studied. Fluorescent spectra were collected through Ocean Optics macros in Excel set to read for 1000 msec integration time and three averages. The spectra were analyzed using the modeled bandpass filters and ratiometric method in Excel to obtain calibration curves for PBS, platelet poor plasma and platelet rich plasma.

Injection molded insert PVC tube assay of fluorescent macromolecular conjugates on porous membrane discs using a custom optimized fluorescence based pH detector. Injection molded polycarbonate parts were fashioned to fix the fluorescent discs to the fluorescence pH detector probe as pictured in FIG. 4. Membranes were prepared as described in the soaking immobilization method in Example 10 and assembled into the plastic insert. A 1 in long and 3/16 in ID PVC tube was placed on the spike end of the insert such that 250 ul of liquid was placed in the tube and covered with parafilm to slow carbon dioxide desorption. A fluorescent measurement of the first and second wavelengths was taken and then the pH was read by a blood gas analyzer (Bayer 348). The pH of plasma samples were adjusted by acid and base additions as in the telescoping tubing insert assay to create the range of pH data.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for measuring the pH of a sample, comprising:
   (a) irradiating a fluorescent species in communication with a sample with excitation light having a wavelength sufficient to effect fluorescent emission from the fluorescent species,
   wherein the fluorescent species comprises a 2-halo seminaphthofluorescein and exhibits a first emission intensity at a first emission wavelength and a second emission intensity at a second emission wavelength, the ratio of the first and second emission intensities being dependent on pH; and
   (b) measuring the first and second emission intensities to determined the pH of the sample.

2. The method of claim 1, wherein the 2-halo seminaphthofluorescein is a 2-chloro seminaphthofluorescein.

3. The method of claim 1, wherein the 2-halo seminaphthofluorescein is 2-(2-chloro-3-hydroxy-9-carboxyethyl-10-oxo-10H-benzo[c]xanthen-7-yl)benzoic acid.

4. The method of claim 1, wherein the 2-halo seminaphthofluorescein is

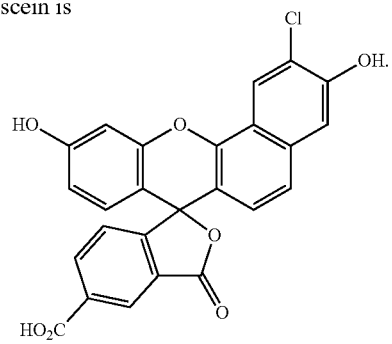

5. The method of claim 1, wherein the fluorescent species is a conjugate of a 2-halo seminaphthofluorescein and a macromolecule.

6. The method of claim 5, wherein the macromolecule is an albumin.

7. The method of claim 5, wherein the macromolecule is a human serum albumin.

8. The method of claim 5, wherein the conjugate is a 2-(2-chloro-3-hydroxy-9-carboxyethyl-10-oxo-10H-benzo[c]xanthen-7-yl)benzoic acid/human serum albumin conjugate.

9. The method of claim 1, wherein the sample comprises blood or a blood product.

10. A system for measuring pH, comprising:
   (a) a light source for exciting a fluorescent species, wherein the fluorescent species comprises a 2-halo seminaphthofluorescein and has a first emission intensity at a first emission wavelength and a second emission intensity at a second emission wavelength;
   (b) a first emission detector for measuring the first emission intensity;
   (c) a second emission detector for measuring the second emission intensity;
   (d) an excitation lightguide for transmitting excitation light from the light source to the fluorescent species, wherein the lightguide comprises a first terminus proximate to the light source and a second terminus distal to the light source;
   (e) a first emission lightguide for transmitting emission from the fluorescent species to the first emission detector, wherein the lightguide comprises a first terminus proximate to the detector and a second terminus distal to the detector;
   (f) a second emission lightguide for transmitting emission from the fluorescent species to the second emission detector, wherein the lightguide comprises a first terminus proximate to the detector and a second terminus distal to the detector;
   (g) a probe housing the distal termini of the excitation lightguide, first emission lightguide, and second emission light guide; and (h) an assembly for receiving the probe, the assembly comprising:
- (i) a housing for receiving the probe, wherein the housing is adapted for receiving the probe at a first end and terminating with a window at the second end, the window being transparent to the excitation and the emission light,
- (ii) a tip member reversibly connectable to the housing's second end, wherein the tip member is adapted to receive liquid from a sample to be measured, and
- (iii) a fluorescent species immobilized on a substrate intermediate the tip member and the window, wherein the fluorescent species immobilized on the substrate is in liquid communication with the sample during the measurement.

11. The system of claim 10, wherein the 2-halo seminaphthofluorescein is a 2-chloro seminaphthofluorescein.

12. The system of claim 10, wherein the 2-halo seminaphthofluorescein is 2-(2-chloro-3-hydroxy-9-carboxyethyl-10-oxo-10H-benzo[c]xanthen-7-yl)benzoic acid.

13. The system of claim 10, wherein the 2-halo seminaphthofluorescein is

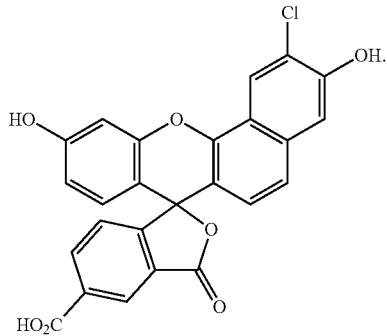

14. The system of claim 10, wherein the fluorescent species is a conjugate of a 2-halo seminaphthofluorescein and a macromolecule.

15. The system of claim 14, wherein the macromolecule is an albumin.

16. The system of claim 14, wherein the macromolecule is a human serum albumin.

17. The system of claim 14, wherein the conjugate is a 2-(2-chloro-3-hydroxy-9-carboxyethyl-10-oxo-10H-benzo[c]xanthen-7-yl)benzoic acid/human serum albumin conjugate.

18. The system of claim 10, wherein the light source is a light-emitting diode.

19. The system of claim 10, wherein the first and second detectors are photodiodes.

20. The system of claim 10, wherein the excitation lightguide, the first emission lightguide, and the second emission lightguide are optical fibers.

21. The system of claim 10, wherein the probe comprises one or more optical fibers.

22. The system of claim 10, wherein the sample comprises blood or a blood product.

23. The system of claim 10, wherein the sample is contained within a sealed vessel.

* * * * *